US006295862B1

(12) United States Patent
Kurokawa et al.

(10) Patent No.: US 6,295,862 B1
(45) Date of Patent: Oct. 2, 2001

(54) GAS CONCENTRATION MEASURING APPARATUS COMPENSATING FOR ERROR COMPONENT OF OUTPUT SIGNAL

(75) Inventors: Eiichi Kurokawa, Okazaki; Tomoo Kawase, Nagoya; Satoshi Hudu, Kariya; Toshiyuki Suzuki, Handa; Satoshi Nakamura, Okazaki, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/432,067

(22) Filed: Nov. 2, 1999

(30) Foreign Application Priority Data

Nov. 2, 1998 (JP) ................................................. 10-312436

(51) Int. Cl.[7] ....................... G01N 27/416; G01N 27/00; G01N 7/00; G01N 27/26; G08B 17/10
(52) U.S. Cl. ...................... 73/31.05; 73/31.02; 73/23.21; 73/23.32; 422/94; 422/90; 204/424; 204/410
(58) Field of Search ............................... 73/31.05, 23.2, 73/23.21, 31.01, 23.32, 23.31, 31.02; 204/406, 410, 421, 424, 425, 427; 422/90, 94, 98

(56) References Cited

U.S. PATENT DOCUMENTS

| 4,443,791 | * | 4/1984 | Risgin et al. ........................ 340/634 |
|---|---|---|---|
| 4,915,813 | * | 4/1990 | Nakajima et al. ................... 204/406 |
| 4,981,125 | * | 1/1991 | Kato et al. .......................... 123/440 |
| 5,270,009 | * | 12/1993 | Nakamori et al. .................... 422/83 |
| 5,686,654 | * | 11/1997 | Friese et al. ........................ 73/23.32 |
| 5,780,715 | * | 7/1998 | Imblum ............................... 73/23.21 |
| 5,866,799 | | 2/1999 | Kato et al. .......................... 73/31.05 |
| 5,942,190 | * | 8/1999 | Kato et al. ............................. 422/98 |
| 6,082,176 | * | 7/2000 | Kondo et al. ........................ 73/23.31 |
| 6,196,053 | * | 3/2001 | Kato et al. .......................... 73/31.05 |
| 6,205,843 | * | 3/2001 | Tanaka et al. ....................... 73/31.06 |
| 6,214,207 | * | 4/2001 | Miyata et al. ....................... 205/781 |

FOREIGN PATENT DOCUMENTS

| 0 798 555 | 10/1997 | (EP) . |
|---|---|---|
| 8-271476 | 10/1996 | (JP) . |
| 9-318596 | 12/1997 | (JP) . |

* cited by examiner

*Primary Examiner*—Hezron Williams
*Assistant Examiner*—David J. Wiggins
(74) *Attorney, Agent, or Firm*—Pillsbury Winthrop LLP

(57) ABSTRACT

A gas concentration measuring apparatus is provided which measures the concentration of two kinds of gas components such as $O_2$ and NOx contained in exhaust gasses of an internal combustion engine of automotive vehicles. The apparatus has a gas sensor which includes a first cell responsive to application of a voltage to discharge $O_2$ in the exhaust gasses to the outside and produce an electric current as a function of concentration of the discharged $O_2$ and a second cell responsive to application of a voltage to produce an electric current as a function of concentration of NOx in the exhaust gasses from which the $O_2$ is discharged by the first cell. The apparatus offsets an error component of the electric current produced by the second cell which depends upon $O_2$ contained in the exhaust gasses, or which in related operations, depends upon any residual oxygen remaining in the second cell without being discharged by the first cell.

17 Claims, 21 Drawing Sheets

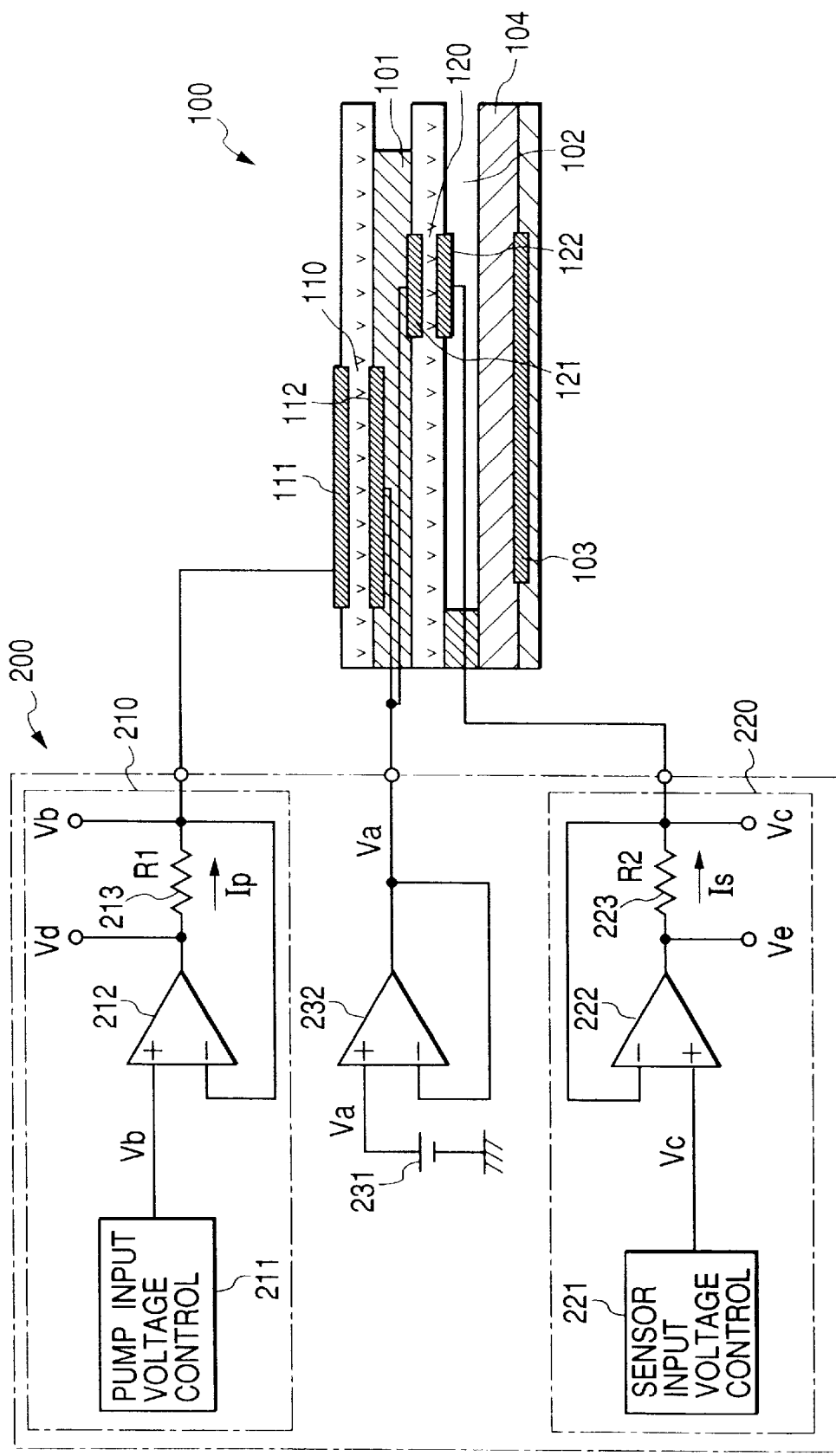

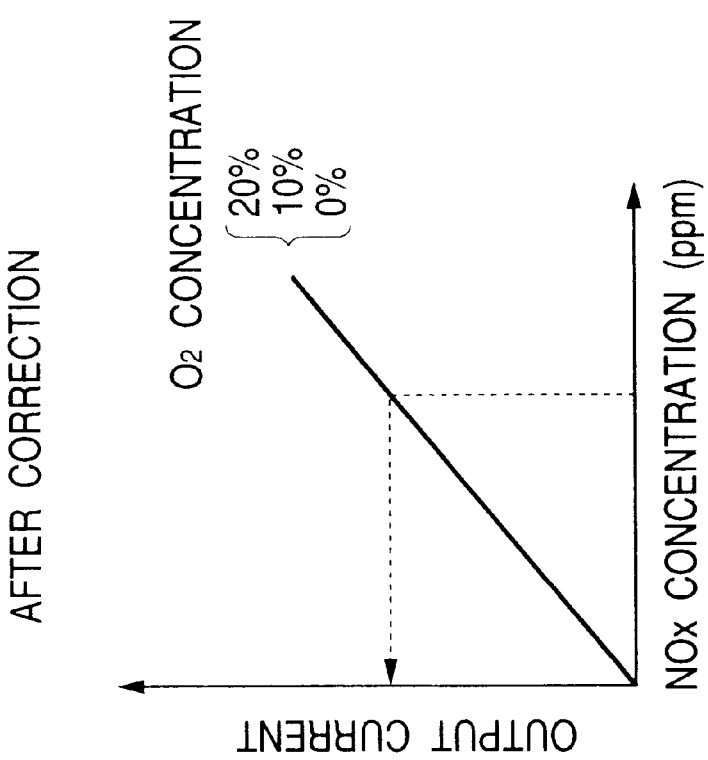
FIG. 11(a) BEFORE CORRECTION
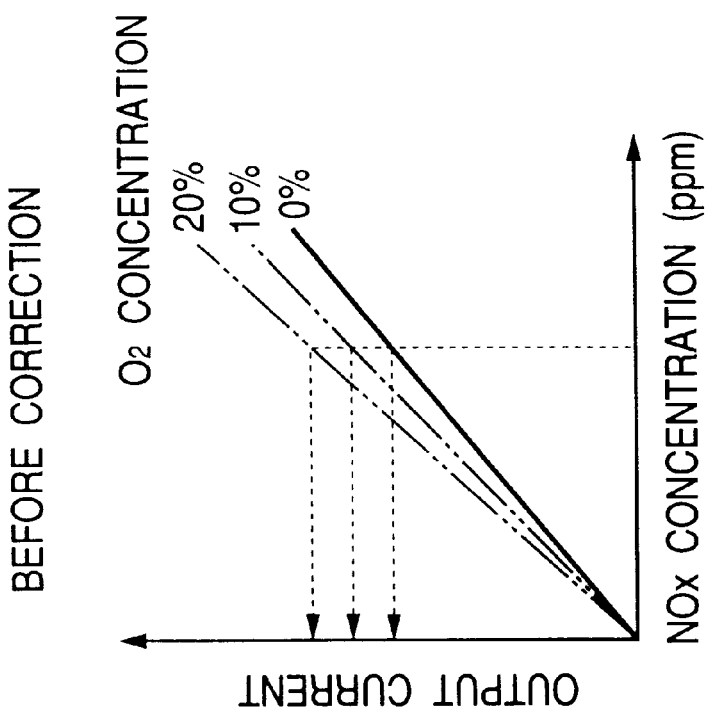
FIG. 11(b) AFTER CORRECTION

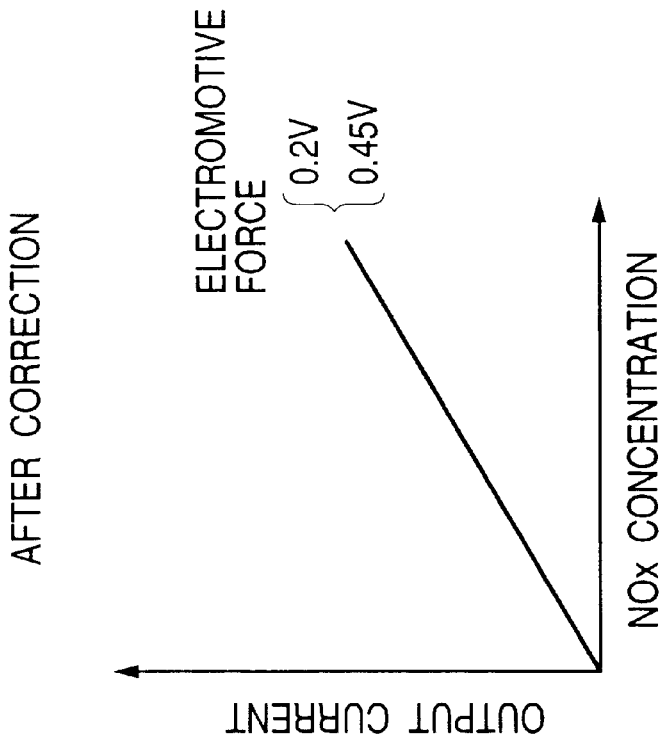
FIG. 26(a) BEFORE CORRECTION
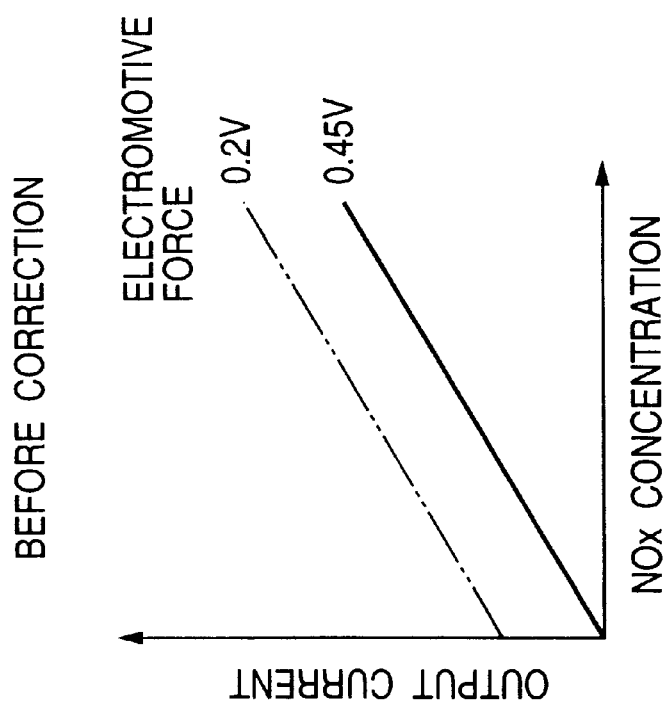
FIG. 26(b) AFTER CORRECTION

US 6,295,862 B1

GAS CONCENTRATION MEASURING APPARATUS COMPENSATING FOR ERROR COMPONENT OF OUTPUT SIGNAL

BACKGROUND OF THE INVENTION

1. Technical Field of the Invention

The present invention relates generally to a gas concentration measuring apparatus for measuring the concentration of gases which may be employed in an air-fuel ratio control system for automotive vehicles, and more particularly to a gas concentration measuring apparatus designed to measure two kinds of gas components and offset an error in measuring one of the gas components which depends upon the other gas component.

2. Background Art

The air pollution caused by exhaust emissions of automotive internal combustion engines is giving rise to a serious problem at the present day. The exhaust emission control standard regulations have been made more rigorous recently. The burning control of gasoline or diesel engines or use of catalyst are, therefore, being studied to reduce pollutants contained in exhaust gasses. In U.S., OBD-II (On Board Diagnostic-II) requirements prescribe that automotive vehicles have a function of determining whether a catalytic converter is operating normally or not.

As one of systems meeting the OBD-II requirements, a two-$O_2$ sensor monitoring system is proposed which monitors outputs of two $O_2$ sensors mounted upstream and downstream of a catalytic converter, respectively, but it is not designed to detect pollutants directly and cannot determine whether pollutants in exhaust gasses have been reduced or not accurately.

If it becomes possible to measure the concentration of NOx in exhaust gasses for monitoring the burning control and the catalytic converter, the pollutants in the exhaust gasses can be reduced greatly. Specifically, the reduction in pollutants in exhaust emissions of the engine is achieved by controlling the quantity of fuel to be injected into the engine and the EGR rate based on the concentration of NOx contained in the exhaust gasses. Additionally, the determination of deterioration of the catalytic converter is achieved easily by installing a NOx sensor downstream of the catalytic converter.

NOx sensors capable of measuring the concentration of NOx accurately and techniques for mounting such NOx sensors in automotive vehicles are, therefore, being sought.

The effects of air-fuel ratio feedback control may be improved further by monitoring the concentration of $O_2$ contained in the exhaust gasses as well as the concentration of NOx. Specifically, modern air-fuel ratio control for automotive vehicles is required to improve the accuracy of the control and perform lean burn engine control. For meeting these requirements, sensors capable of determining the air-fuel ratio of a mixture supplied to the engine over a wide range are being sought.

U.S. Pat. No. 5,866,799 teaches a NOx sensor designed to reduce the quantity of $O_2$ contained in exhaust gasses first and then measure the concentration of NOx in the exhaust gasses. The measurement of concentration of NOx is achieved by decomposing NOx gas components into oxygen ions and measuring an electric current produced by the flow of the oxygen ions through electrodes. This type of NOx sensor, however, has the drawback in that the part of $O_2$ gas contained in the exhaust gasses entering the sensor reaches the electrodes for measuring the concentration NOx, which causes an error component to be produced in the current indicative of the concentration of NOx. This problem will also be referred to in detail later in description of embodiments of the invention.

SUMMARY OF THE INVENTION

It is therefore a principal object of the present invention to avoid the disadvantages of the prior art.

It is another object of the present invention to provide a gas concentration measuring apparatus designed to measure two kinds of gas components and offset an error in measuring one of the gas components which depends upon the other gas component.

According to one aspect of the invention, there is provided a gas concentration measuring apparatus which comprises: (a) a gas concentration sensor including a diffused resistor into which gasses flow, a first cell responsive to application of a voltage to discharge oxygen contained in the gasses outside the gas concentration sensor, producing a first electric current as a function of concentration of the discharged oxygen, and a second cell responsive to application of a voltage to produce a second electric current as a function of concentration of a specified gas component contained in the gasses from which the oxygen is discharged by the first cell; (b) a first current measuring circuit measuring the first electric current flowing through the first cell of the gas concentration sensor; (c) a second current measuring circuit measuring the second electric current flowing through the second cell of the gas concentration sensor; and (d) a correcting circuit correcting the second electric current measured by the second current measuring circuit based on the first electric current measured by the first current measuring circuit to compensate for an oxygen-caused error component of the second electric current which depends upon the concentration of oxygen in the gasses and provide an error-corrected second electric current.

In the preferred mode of the invention, if the first electric current is defined as Ip and the second electric current is defined as Is, the correcting circuit provides the error-corrected second electric current Isf according to the following equation:

$$Isf = Is \cdot Kb / (Ka \cdot Ip + Kb)$$

where Ka is a structural constant defined by a structure of the gas concentration sensor, and Kb is a correction coefficient defined by sensitivity of the second cell.

The structural constant Ka is determined by a diffusion coefficient, a shape, and a volume of the diffused resistor, and locations of the first and second cell in the gas concentration sensor.

The correcting circuit stores correction data representing a relation between the concentration of oxygen in the gasses and the oxygen-caused error component of the second electric current and monitors the first electric current to determine the error-corrected second electric current based on the correction data.

The correction data is so defined that the concentration of the specified gas component indicated by the second electric current is decreased as the concentration of oxygen indicated by the first electric current increases.

According to the second aspect of the invention, there is provided a gas concentration measuring apparatus which comprises: (a) a gas concentration sensor including a diffused resistor into which gasses flow, a first cell responsive to application of a voltage to discharge oxygen contained in the gasses outside the gas concentration sensor, producing a first electric current as a function of concentration of the discharged oxygen, and a second cell responsive to application of a voltage to produce a second electric current as a function of concentration of a specified gas component contained in the gasses from which the oxygen is discharged by the first cell; and (b) a correcting circuit correcting the second electric current flowing through the second cell to compensate for a residual oxygen-caused error component contained in the second electric current which depends upon a quantity of oxygen remaining on the second cell without being discharged by the first cell.

In the preferred mode of the invention, an offset current measuring circuit is further provided which measures an offset current flowing through the second cell as a function of the quantity of oxygen remaining on the second cell. The correcting circuit compensates for the residual oxygen-caused error component based on the offset current.

The second cell is so designed as to produce the offset current plus the second electric current in response to the application of the voltage in a first voltage level range and only the offset current in response to the application of the voltage in a second voltage level range different from the first voltage level range. The offset current measuring circuit applies the voltage within the second voltage level range to the second cell to measure the offset current.

The correcting circuit may apply the voltage within the first voltage level range to the second cell to measure the second electric current and apply the voltage within the second voltage level range to the second cell to measure the offset current. The correcting circuit compensates for the residual oxygen-caused error component based on the offset current.

A switching circuit is further provided which switches between a first and a second voltage application mode. In the first voltage application mode, the voltage in the first voltage level range is applied to the second cell. In the second voltage application mode, the voltage in the second voltage level range is applied to the second cell.

An electromotive force measuring circuit may alternatively be provided which measures an electromotive force produced by the second cell as a function of the quantity of oxygen remaining on the second cell. The correcting circuit offsets the residual oxygen-caused caused error component of the second electric current based on the electromotive force measured by the electromotive force measuring circuit.

The electromotive force measuring circuit includes a switch which is turned on to block communication between the second cell of the gas concentration sensor and a voltage source applying the voltage to the second cell. The electromotive force measuring circuit measures the electromotive force when the switch is turned on.

According to the third aspect of the invention, there is provided a gas concentration measuring apparatus which comprises: (a) a gas concentration sensor including a diffused resistor into which gasses flow, a first cell responsive to application of a voltage to discharge oxygen contained in the gasses outside the gas concentration sensor, producing a first electric current as a function of concentration of the discharged oxygen, and a second cell responsive to application of a voltage to produce a second electric current as a function of concentration of a specified gas component contained in the gasses from which the oxygen is discharged by the first cell; (b) a first current measuring circuit measuring the first electric current flowing through the first cell of the gas concentration sensor; (c) a second current measuring circuit measuring the second electric current flowing through the second cell of the gas concentration sensor; and (d) a correcting circuit performing a first correcting operation and a second correcting operation, the first correcting operation correcting the second electric current measured by the second current measuring circuit based on the first electric current measured by the first current measuring circuit to compensate for an oxygen-caused error component of the second electric current which depends upon the concentration of oxygen in the gasses, the second correcting operation correcting the second electric current to compensate for a residual oxygen-caused error component contained in the second electric current which depends upon a quantity of oxygen remaining on the second cell without being discharged by the first cell.

In the preferred mode of the invention, the correcting circuit selectively performs the first and second correcting operations according to given requirements of the first and second correcting operations.

The first and second current measuring circuits measure the first and second electric currents in a cycle. The correcting circuit performs the first correcting operation in a first cycle shorter than a second cycle in which the second correcting operation is performed.

According to the fourth aspect of the invention, there is provided a gas concentration sensor which comprises: (a) a diffused resistor into which gasses flow; (b) a first cell responsive to application of a voltage to discharge oxygen contained in the gasses outside the gas concentration sensor, producing a first electric current as a function of concentration of the discharged oxygen; and (c) a second cell responsive to application of a voltage to produce a second electric current as a function of concentration of a specified gas component contained in the gasses from which the oxygen is discharged by the first cell, the second cell being so designed as to produce an offset current plus the second electric current in response to the application of the voltage in a first voltage level range and only the offset current in response to the application of the voltage in a second voltage level range different from the first voltage level range.

Each of the first and second cell includes a first electrode exposed to the diffused resistor and a second electrode located away from the diffused resistor. The first electrode of the first and second cells are made of a material which is inactive with respect to the specified gas component.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 2 is an illustration which shows structures of a gas concentration sensor and a sensor controller;

FIG. 11 (a) is a graph which shows an output current of a NOx current correction circuit before a NOx current is corrected;

FIG. 11 (b) is a graph which shows an output current of a NOx current correction circuit after a NOx current is corrected;

FIG. 26(a) is a graph which shows an output current of a NOx current correction circuit before a NOx current is corrected;

FIG. 26(b) is a graph which shows an output current of a NOx current correction circuit after a NOx current is corrected;

DESCRIPTION OF THE PREFERRED EMBODIMENTS

Figure 1:
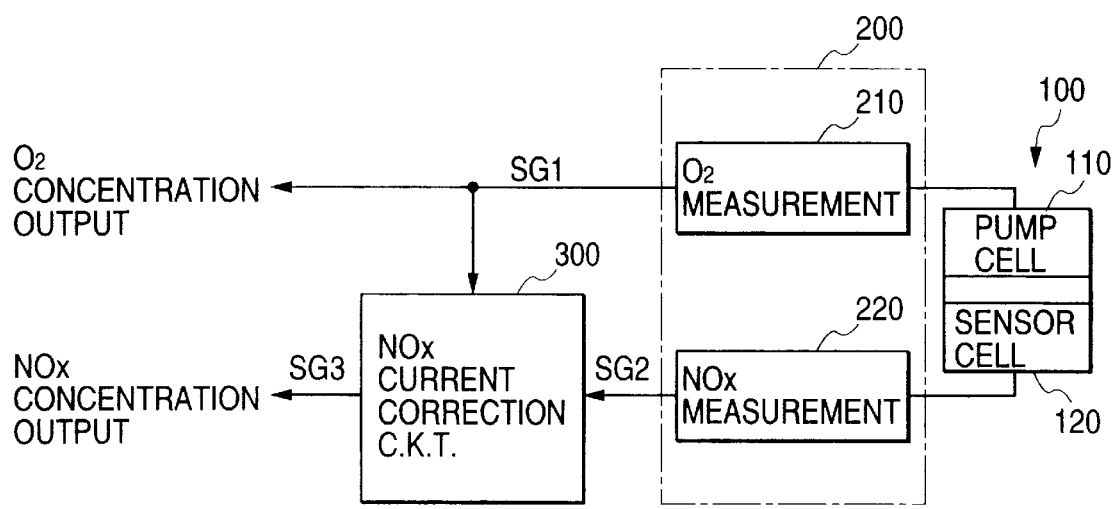
FIG. 1 is a block diagram which shows a gas concentration measuring apparatus according to the first embodiment of the invention.

Referring now to the drawings, wherein like numbers refer to like parts in several views, particularly to FIG. 1, there is shown a gas concentration measuring apparatus according to the first embodiment of the invention which is used with an automotive control system designed to control the quantity of fuel injected into an internal combustion gasoline engine as a function of an output of the gas concentration measuring apparatus under feedback (F/B) control to bring the air-fuel (A/F) ratio into agreement with a target value. The gas concentration measuring apparatus uses a composite gas sensor capable of measuring concentrations of an oxygen ($O_2$) and nitrogen oxide (NOx) contained in exhaust gasses of the internal combustion engine simultaneously.

The output of the gas concentration measuring apparatus is also used in the control system to control a NOx catalytic converter (e.g., a NOx adsorption reduction catalytic converter) mounted in an exhaust pipe of the engine. Specifically, the control system determines the amount of NOx discharged from the NOx catalytic converter without being reacted or purified using an output of the gas concentration measuring apparatus and recovers the ability of NOx catalytic converter if the discharged amount of NOx increases. Such recovery is achieved by supplying an enriched mixture to the NOx catalytic converter temporarily to remove ions adsorbed in the NOx catalytic converter.

The gas concentration measuring apparatus, as shown in FIG. 1, generally includes a gas concentration sensor 100, a sensor controller 200, and a NOx current correction circuit 300.

The gas concentration sensor 100 is installed in, for example, an exhaust pipe of the engine and includes a pump cell 110 for measuring the concentration of $O_2$ and a sensor cell 120 for measuring the concentration of NOx.

The sensor controller 200 includes an oxygen concentration determining circuit 210 and a NOx concentration determining circuit 220. The oxygen concentration determining circuit 210 is connected to the pump cell 110 of the gas concentration sensor 100 to apply the voltage thereto and measure an electric current flowing through the pump cell 110 as a function of the concentration of $O_2$ and outputs a sensor signal SG1 indicative of the concentration of $O_2$ to the NOx current correction circuit 300 and the automotive control system for controlling the air-fuel ratio of mixture supplied to the engine. The NOx concentration determining circuit 220 is connected to the sensor cell 120 to apply the voltage thereto and measure an electric current flowing through the sensor cell 120 as a function of the concentration of NOx and outputs a sensor signal SG2 indicative of the concentration of NOx to the NOx current correction circuit 300.

The NOx current correction circuit 300 receives the sensor signals SG1 and SG2 from the oxygen concentration determining circuit 210 and the NOx concentration measuring circuit 220 and offsets an error component of the SG2 which depends upon the concentration of $O_2$ to output the error-corrected sensor signal SG2 as a signal SG3 to the automotive control circuit.

Figure 3:
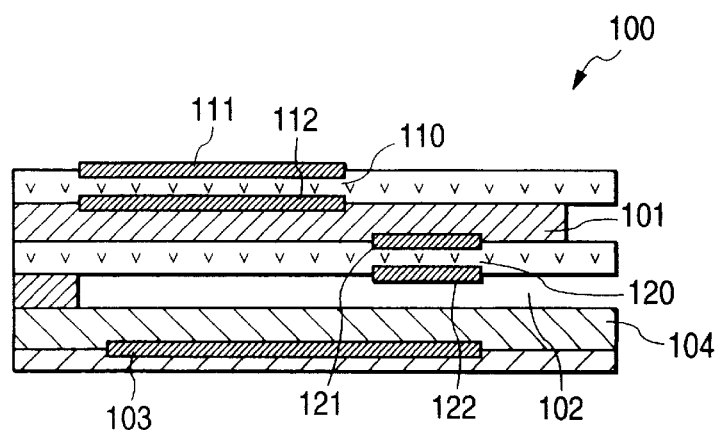
FIG. 3 is a sectional view which shows an internal structure of a gas concentration sensor.

The gas concentration sensor 100 has, as shown in FIG. 3, a two-cell structure designed to measure concentrations of $O_2$ and NOx contained in exhaust gasses of the internal combustion engine simultaneously. The gas concentration sensor 100 is made of a lamination of the pump cell 110, the sensor cell 120, a porous diffused layer 101, an air duct 102, an insulating layer 104, and a heater 103. The gas concentration sensor 100 is installed at the right side thereof, as viewed in the drawing, on an exhaust pipe of the engine so as to expose upper, lower, and left surfaces to exhaust gasses.

The pump cell 110 is disposed on the porous diffused layer 101 so that it is exposed to the exhaust gasses. A first pump electrode 111 is mounted on the upper surface of the pump cell 110. A second pump electrode 112 is mounted on the lower surface thereof facing the porous diffused layer 101. The sensor cell 120 is interposed between the porous diffused layer 101 and the air duct 102. A first sensor cell electrode 121 is attached to an upper surface of the sensor cell 120 facing the porous diffused layer 101. A second sensor cell electrode 122 is attached to a lower surface of the sensor cell 120 facing the air duct 102. The exhaust gasses enters the porous diffused layer 101 from the left side thereof, as viewed in the drawing, and flow in the right direction.

The pump cell 110 and the sensor cell 120 are each formed with a solid electrolyte lamination such as an oxygen ion conductive oxide sintered member made from $ZrO_2$, $HfO_2$, $ThO_2$, and $Bi_2O_3$ in which CaO, MgO, $Y_2O_3$, and $Yb_2O_3$ are solved as fixing agents. The porous diffused layer 101 is made of a heat-resisting inorganic matter such as alumina, magnesia, silica, spinel, and mullite.

The first pump cell electrode 111 and the first and second sensor cell electrodes 121 and 122 are each made of a noble metal with a high catalytic activity such as platinum, while the second pump electrode 112 is made of a noble metal such as Au-Pt which is inactive with respect to NOx, that is, hardly decomposes NOx.

The heater 103 is embedded in the insulating layer 104. The insulating layer 104 defines the air duct 102 between itself and the sensor cell 120. The air duct 102 serves as a reference gas chamber into which the air is introduced. The air in the reference gas chamber is used as a reference gas in measuring the concentration of $O_2$. The insulating layer 104 is made of alumina. The heater 103 is made of platinum and cermet such as alumina and supplied with power from the sensor controller 200 to produce the heat for activating the whole of the gas concentration sensor 100.

Figure 4A:
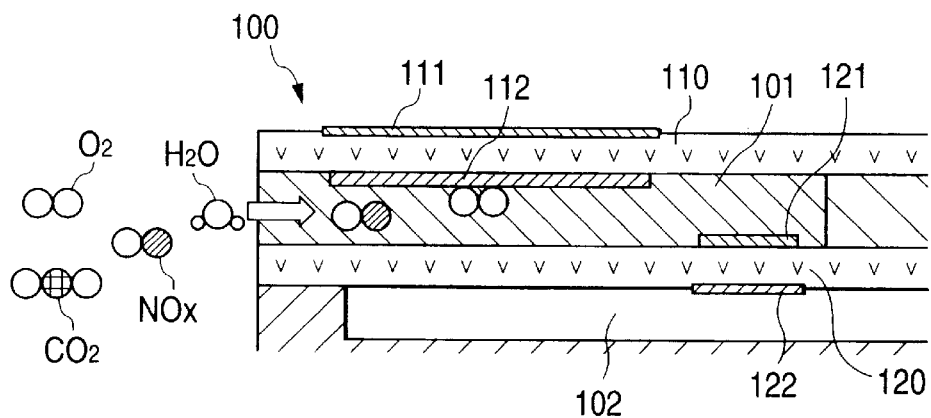
FIGS. 4(a), 4(b), and 4(c) are sectional views which show a sequence of gas measurement operations of a gas concentration sensor.
Figure 4B:
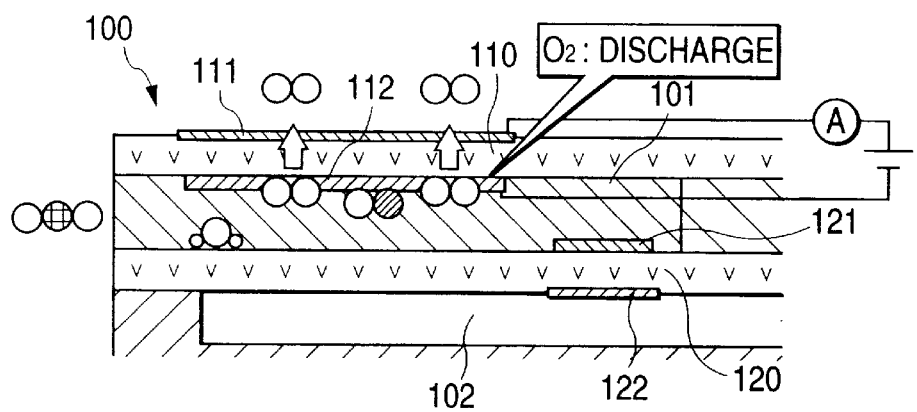

In operation, when exhaust gasses containing $O_2$, NOx, $CO_2$, and $H_2O$ enter, as shown in FIG. 4(a), the porous diffused layer 101 and are passing the pump cell 110, application of voltage to the pump cell 110 through the electrodes 111 and 112 causes the exhaust gasses to undergo decomposition. Since the second pump cell electrode 112 is, as described above, made of a noble metal which hardly decomposes NOx, only $O_2$ molecules contained in the exhaust gasses are decomposed or ionized by the pump cell 100, as shown in FIG. 4(b), which are, in turn, returned to the exhaust gasses from the first pump cell electrode 111, thereby causing a limiting current (also referred to as a pump cell current below) to flow through the pump cell 110 as a function of the concentration of $O_2$ in the exhaust gasses, which is, in turn, picked up by the oxygen concentration measuring circuit 210.

Figure 4C:
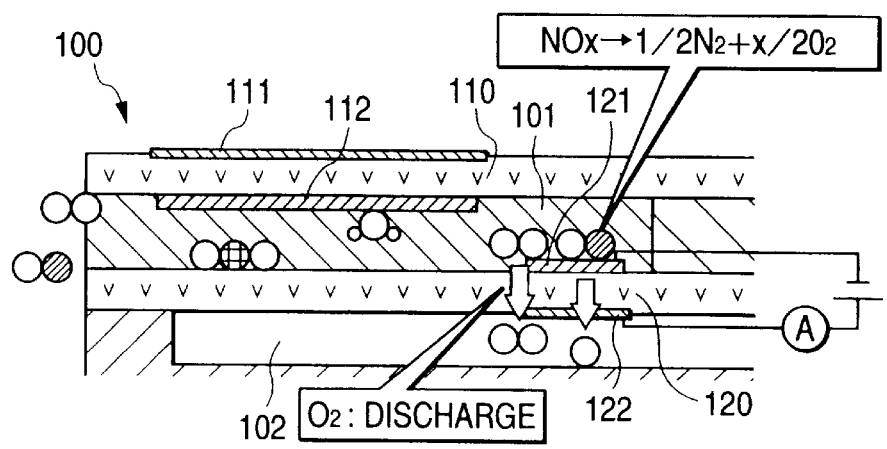

The $O_2$ molecules in the exhaust gasses are usually not decomposed by the pump cell 110 completely, so that residual $O_2$ molecules reach the sensor cell 120. The application of voltage to the sensor cell 120 causes the first sensor cell electrode 121 to decompose the $O_2$ and NOx molecules, as shown in FIG. 4(c), so that oxygen ions are discharged to the air duct 102 through the second sensor cell electrode 122, thereby causing a limiting current (also referred to as a sensor cell current or a NOx current below) to flow through the sensor cell 120 as a function of the concentration of NOx, which is, in turn, picked up by the NOx concentration measuring circuit 220. The NOx current inputted to the NOx concentration measuring circuit 220 contains a current component produced by decomposition of the $O_2$ molecules remaining in the exhaust gasses which is used as an offset current in determining the concentration of NOx using the sensor cell current.

Figure 5:
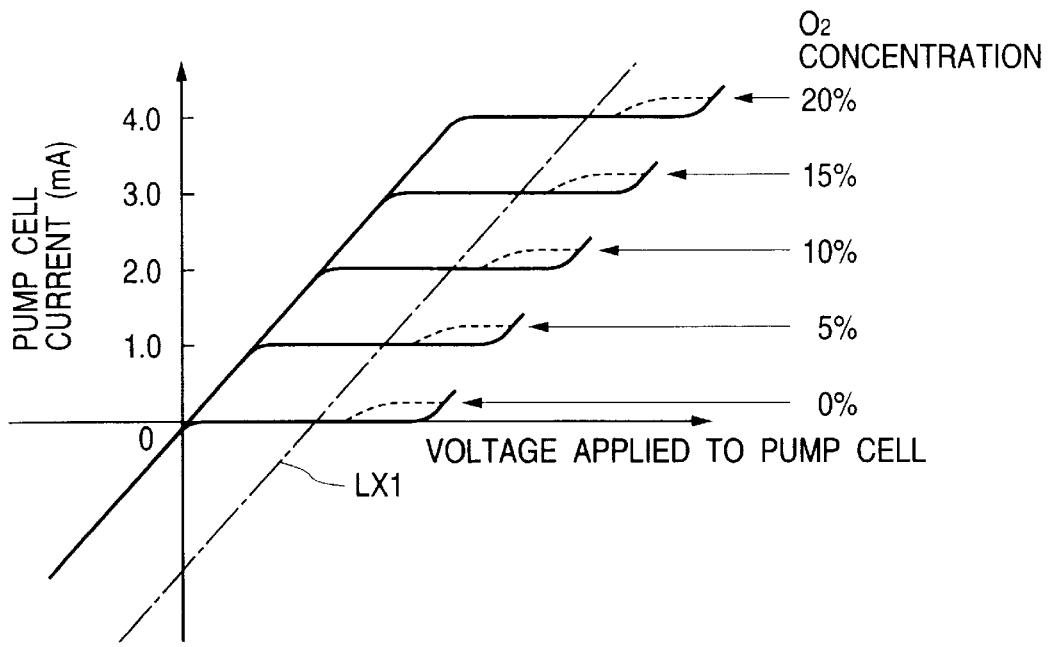
FIG. 5 is a graph which shows a relation between a pump cell current produced by a pump cell and a voltage applied to the pump cell.

FIG. 5 shows a V–I relation between the voltage applied to the pump cell 110 and the pump cell current (mA) outputted from the pump cell 110. Straight segments of lines extending parallel to the abscissa axis indicate limiting current measurable ranges, respectively, which are shifted to the positive side of voltage applied to the pump cell 110 as the concentration of $O_2$ increases. Therefore, if the voltage applied to the pump cell 110 is kept constant when the concentration of $O_2$ is changing, the concentration of $O_2$ may exceed a corresponding one of the limiting current measurable ranges, resulting in difficulty in measuring the concentration of $O_2$ accurately. This also means that a large quantity Of $O_2$ reaches the sensor cell 120 without being discharged from the pump cell 110, thereby causing an error component contained in the NOx current to be increased. In order to avoid this, the voltage to be applied to the pump cell 110 is regulated so that it changes at a rate equivalent to a rate of change in dc resistance component of the pump cell 110 as a function of the voltage applied to the pump cell 110. Specifically, the voltage to be applied to the pump cell 110 is changed along a broken line LX1 so that an output of the pump cell 110 may fall within any one of the limiting current measurable ranges at all the time regardless of the concentration of $O_2$ in the exhaust gasses. The second pump cell electrode 112 of the pump cell 110 is, as described above, made of material which hardly decomposes NOx, so that NOx molecules in the exhaust gasses are hardly decomposed, but if the voltage applied to the pump cell 110 exceeds a certain upper limit in each limiting current measurable range, it will cause the NOx molecules to be decomposed, thereby producing an error, as indicated by a broken curved line, in the limiting current outputted from the pump cell 110. The voltage line LX1 is, therefore, so selected as to pass below the upper limit in each of the limiting current measurable ranges.

Figure 6:
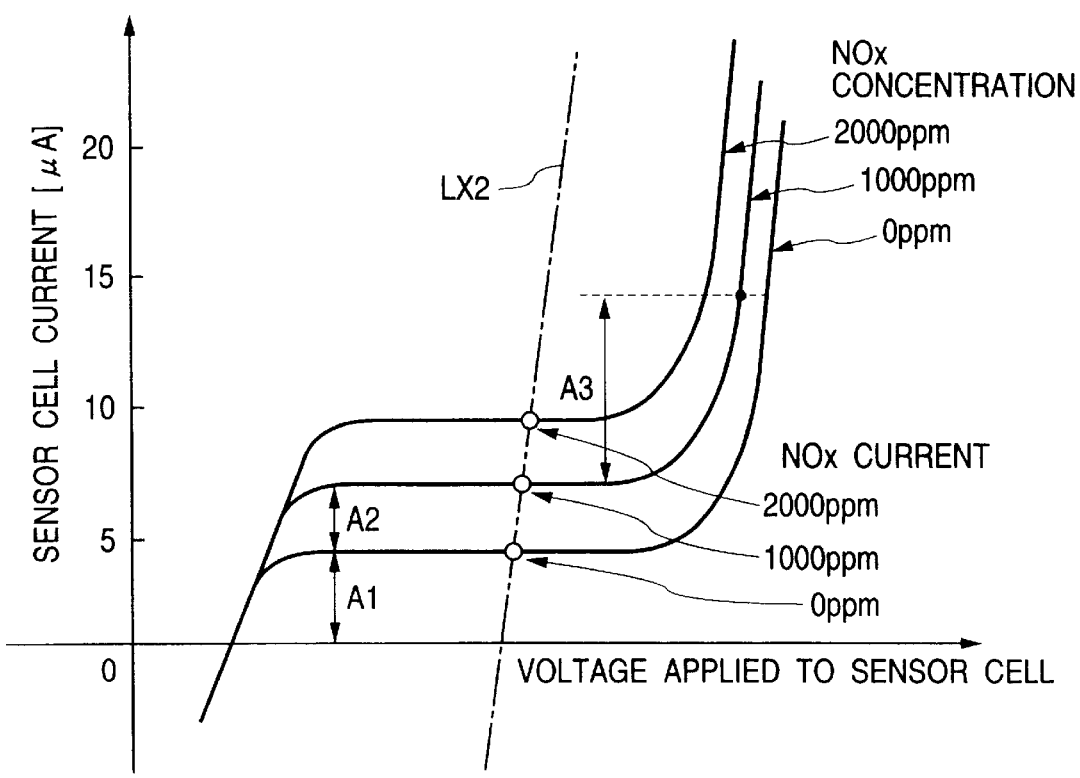
FIG. 6 is a graph which shows a relation between a sensor cell current flowing through a sensor cell and a voltage applied to the sensor cell.

FIG. 6 shows a V–I relation between the voltage applied to the sensor cell 120 and the sensor cell current (mA) outputted from the sensor cell 120. In a range where the concentration of NOx is zero (0) ppm, only a current, as indicated by A1, produced by the residual $O_2$ molecules flowing through the porous diffused layer 101 to the sensor cell 120 is outputted from the sensor cell 120 as the offset current. In a range where the concentration of NOx is greater than zero (0) and smaller than 1,000 ppm, a current, as indicated by A2, produced by the decomposition of NOx by the sensor cell 120 is also outputted from the sensor cell 120. If the voltage applied to the sensor cell 120 exceeds a certain upper limit, it will cause an additional current, as indicated by A3, produced by decomposition of $H_2O$ to be also outputted from the sensor cell 120. Straight segments of lines extending parallel to the abscissa axis indicate limiting current measurable ranges, respectively, where it is possible to measure the NOx decomposition-produced current and which are slightly shifted to the positive side of voltage applied to the sensor cell 120 as the concentration of NOx increases. The voltage applied to the sensor cell 120 is, therefore, controlled along a broken line LX2 so that an output of the sensor cell 120 may fall within one of the limiting current measurable ranges at all the time regardless of the concentration of NOx in the exhaust gasses.

Returning back to FIG. 2, there is shown a circuit structure of the sensor controller 200.

The polarities of the first and second pump cell electrodes 111 and 112 of the pump cell 110 are determined based on the direction of the pump cell current Ip flowing when a lean gas is introduced into the porous diffused layer 101 of the gas concentration sensor 100, and an excess of oxygen is discharged through the pump cell 110. In the shown structure, the first pump cell electrode 111 is connected to a positive terminal of the sensor controller 200, while the second pump cell electrode 112 is connected to a common negative terminal of the sensor controller 200. Similarly, the polarities of the first and second sensor cell electrodes 121 and 122 of the sensor cell 120 are determined based on the direction of the sensor cell current Is flowing when a lean gas is introduced into the porous diffused layer 101 of the gas concentration sensor 100. In the shown structure, the first sensor cell electrode 121 is connected to the common negative terminal of the sensor controller 200, while the second sensor cell electrode 122 is connected to a positive terminal of the sensor controller 200.

The sensor controller 200 includes a reference voltage circuit 231 and an amplifier 232. The reference voltage circuit 231 provides through the amplifier 232 a reference voltage to the common negative terminal connecting with the second pump electrode 112 and the first sensor cell electrode 121. Specifically, the reference voltage circuit 231 produces the voltage Va and inputs it to a non-inverting input of the amplifier 232. The amplifier 232 connects at an output to an inverting input thereof to have a voltage follower structure and applies the voltage Va to the second pump cell electrode 112 and the first sensor cell electrode 121 to keep them above a GND potential (i.e., 0V). This allows a negative current to flow through each of the pump cell 110 and the sensor cell 120. For example, when Va>Vc (>Ve), it will cause the pump cell current Ip and the sensor cell current Is to have a negative value. Thus, even when a rich gas which usually reduces a flow of the negative current and changes a balance of concentration of $O_2$ in the porous diffused layer 101, enters the gas concentration sensor 100, it becomes possible to keep the concentration of gas, for example, of $O_2$ in the porous diffused layer 101 at a constant value equivalent to the stoichiometric. This enables the rich gas to be measured accurately, thus resulting in an increase in measurable range of the gas concentration sensor 100 and also results in greatly improved response rate of the gas concentration sensor 100 when the gas returns from the rich to lean side.

The oxygen concentration determining circuit 210 includes a pump input voltage control circuit 211, an ampli-fier 212, and a resistor 213. The pump input voltage control circuit 211 controls the voltage to be applied to the pump cell 110 along the voltage line LX1 shown in FIG. 5 according to the pump cell current Ip. Specifically, the pump input voltage control circuit 211 provides a control voltage Vb to an non-inverting input of the amplifier 212. An output of the amplifier 212 is connected to one end of the resistor 213 used in measuring the pump cell current Ip. The other end of the resistor 213 is connected to the first pump cell electrode 111 and an inverting input of the amplifier 212, thereby controlling the voltage appearing at the first pump cell electrode 111 to be kept at the same potential as the control voltage Va developed by the pump input voltage control circuit 211.

An output voltage of the amplifier 212 is inputted to the pump input voltage control circuit 211 through a terminal Vd. The voltage appearing at the first pump cell electrode 111 is inputted to the pump input voltage control circuit 211 through a terminal Vb. The voltages at the terminal Vd and Vb are also inputted as the signal SG1 to the NOx current correction circuit 300 as shown in FIG. 1.

The pump cell input voltage Vp and the pump cell current Ip are given by the following equations.

$$Vp=Vb-Va$$

$$Ip=(Vd-Vb)/R1$$

where Vb and Vd are voltages appearing at the terminals Vb and Vd, and R1 is a resistance value of the resistor 213.

The NOx concentration determining circuit 220 includes a sensor input voltage control circuit 221, an amplifier 222, and a resistor 223. The sensor input voltage control circuit 221 controls the voltage to be applied to the sensor cell 120 along the input voltage line LX2 shown in FIG. 6 according to the sensor cell current Is. Specifically, the sensor input voltage control circuit 221 provides a control voltage Vc to an non-inverting input of the amplifier 222. An output of the amplifier 222 is connected to one end of the resistor 223 used in measuring the sensor cell current Is. The other end of the resistor 223 is connected to the second sensor cell electrode 122 and an inverting input of the amplifier 222, thereby controlling the voltage appearing at the second sensor cell electrode 122 to be kept at the same potential as the control voltage Vc developed by the sensor input voltage control circuit 221.

An output voltage of the amplifier 222 is inputted to the sensor input voltage control circuit 221 through a terminal Ve. The voltage appearing at the second sensor cell electrode 122 is inputted to the sensor input voltage control circuit 221 through a terminal Vc. The voltages at the terminal Ve and Vc are also inputted as the signal SG2 to the NOx current correction circuit 300 as shown in FIG. 1.

The sensor cell input voltage Vs and the pump cell current Is are given by the following equations.

$$Vs=Vc-Va$$

$$Is=(Ve-Vc)/R2$$

where Ve and Vc are voltages appearing at the terminals Ve and Vc, and R2 is a resistance value of the resistor 223.

Figure 7:
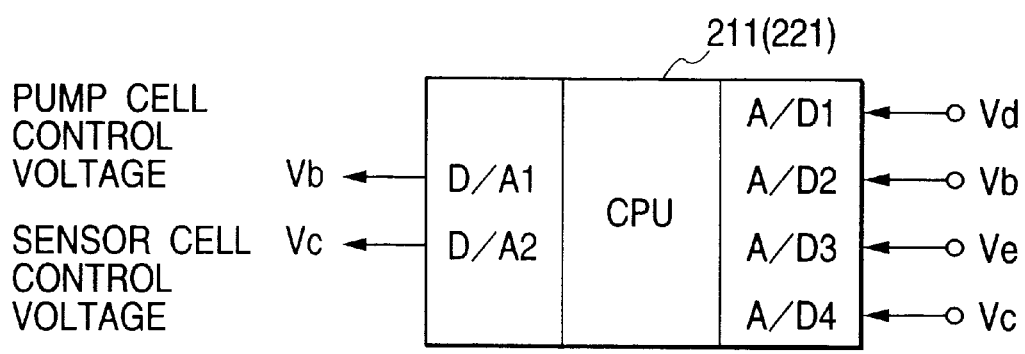
FIG. 7 is an illustration of a structure of each of an $O_2$ concentration determining circuit and a NOx concentration measuring circuit.

The pump input voltage control circuit 211 and the sensor input voltage control circuit 221 are built in a single microcomputer which includes, as shown in FIG. 7, a CPU, two D/A converters D/A 1 and D/A2, and four A/D converters A/D1 to A/D4. The four A/D converters are connected to the terminals Vd, Vb, Ve, and Vc, as shown in FIG. 2, respectively. The two D/A converters output the control voltages Vb and Vc to the amplifiers 212 and 222, respectively.

Figure 9:
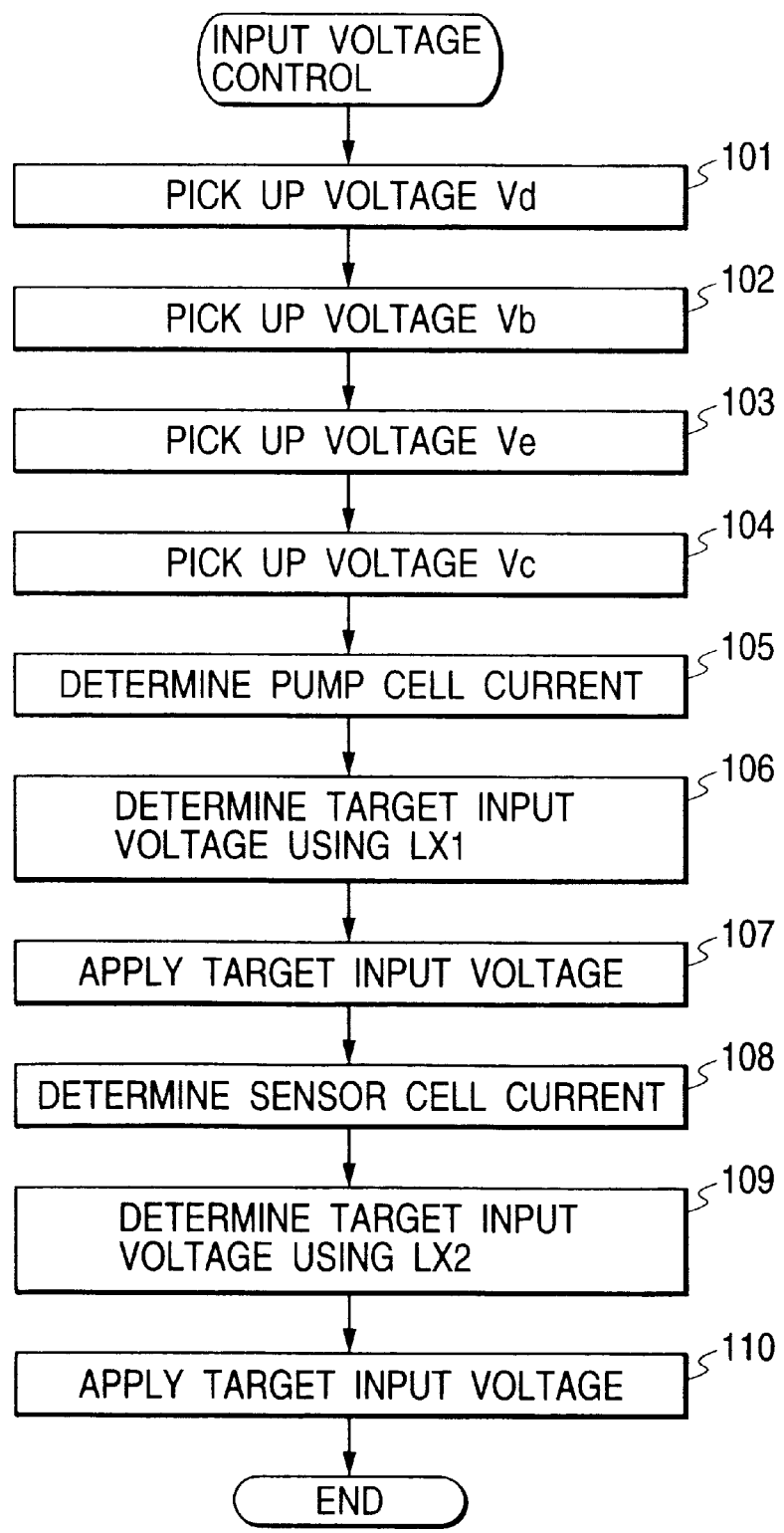
FIG. 9 is a flowchart of a program performed to control a voltage applied to a sensor cell of a gas concentration sensor.

FIG. 9 shows an input voltage control subroutine performed by the CPU installed in the microcomputer shown in FIG. 7 in the course of execution of a main program (not shown), for example, an air-fuel ratio control program.

First, in step 101, the CPU picks up the voltage Vd which is developed at the terminal Vd (i.e., one end of the resistor 213) and converted into a digital signal through the A/D converter A/D1. Similarly, in steps 102, 103, and 104, the CPU picks up the voltages Vb, Ve, and Vc which are developed at the terminals Vc, Ve, and Vc and converted into digital signals through the A/D converters A/D2 to A/D4, respectively.

After step 104, the routine proceeds to step 105 wherein the pump cell current Ip (=(Vd−Vb)/R1) is determined. The routine proceeds to step 106 wherein a target input voltage to be applied to the pump cell 110 is determined which corresponds to the pump cell current Ip on the voltage line LX1 shown in FIG. 5. The routine proceeds to step 107 wherein the target input voltage determined in step 106 is outputted as the pump cell control voltage Vb through the D/A converter D/A1.

The routine proceeds to step 108 wherein the sensor cell current Is (=(Ve−Vc)/R2) is determined. The routine proceeds to step 109 wherein a target input voltage to be applied to the sensor cell 120 is determined which corresponds to the sensor cell current Is on the voltage line LX2 shown in FIG. 6. The routine proceeds to step 110 wherein the target input voltage determined in step 109 is outputted as the sensor cell control voltage Vc through the D/A converter D/A2, after which the routine terminates.

Figure 8:
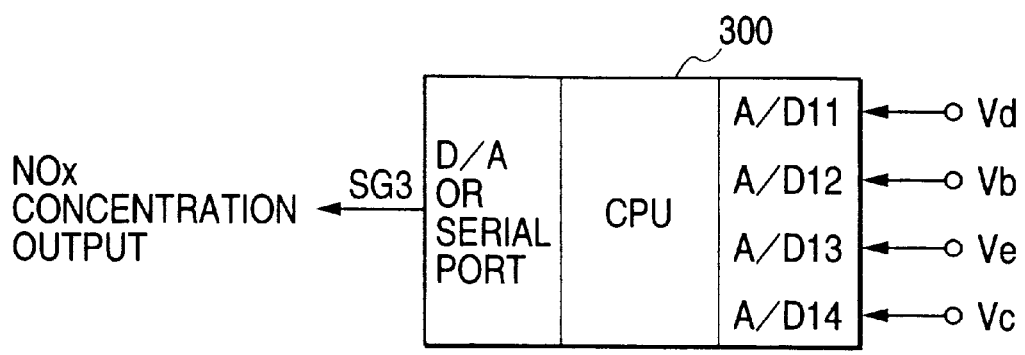
FIG. 8 is an illustration of a structure of a NOx current correction circuit.

The NOx current correction circuit 300 is, as shown in FIG. 8, made of a microcomputer consisting of a CPU, a D/A converter D/A, and four A/D converters A/D11 to A/D14. The four A/D converters are connected to the terminals Vd, Vb, Ve, and Vc, as shown in FIG. 2, respectively. The CPU determines the pump cell current Ip and the sensor cell current Is based on the voltages appearing at the terminals Vd, Vb, Ve, and Vc, to correct the sensor cell current Is using the pump cell current Ip for compensating for an error component produced by the oxygen contained in an excess of NOx flowing from the outside of the porous diffused layer 101 resulting from discharge of $O_2$ outside the pump cell 110 (also referred to as an oxygen-caused error component below) and outputs the corrected sensor cell current Isf as the signal SG3 through the D/A converter or a serial output port. The NOx current correction circuit 300 may alternatively be built in the microcomputer shown in FIG. 7 together with the pump input voltage control circuit 211 and the sensor input voltage control circuit 221.

Figure 10:
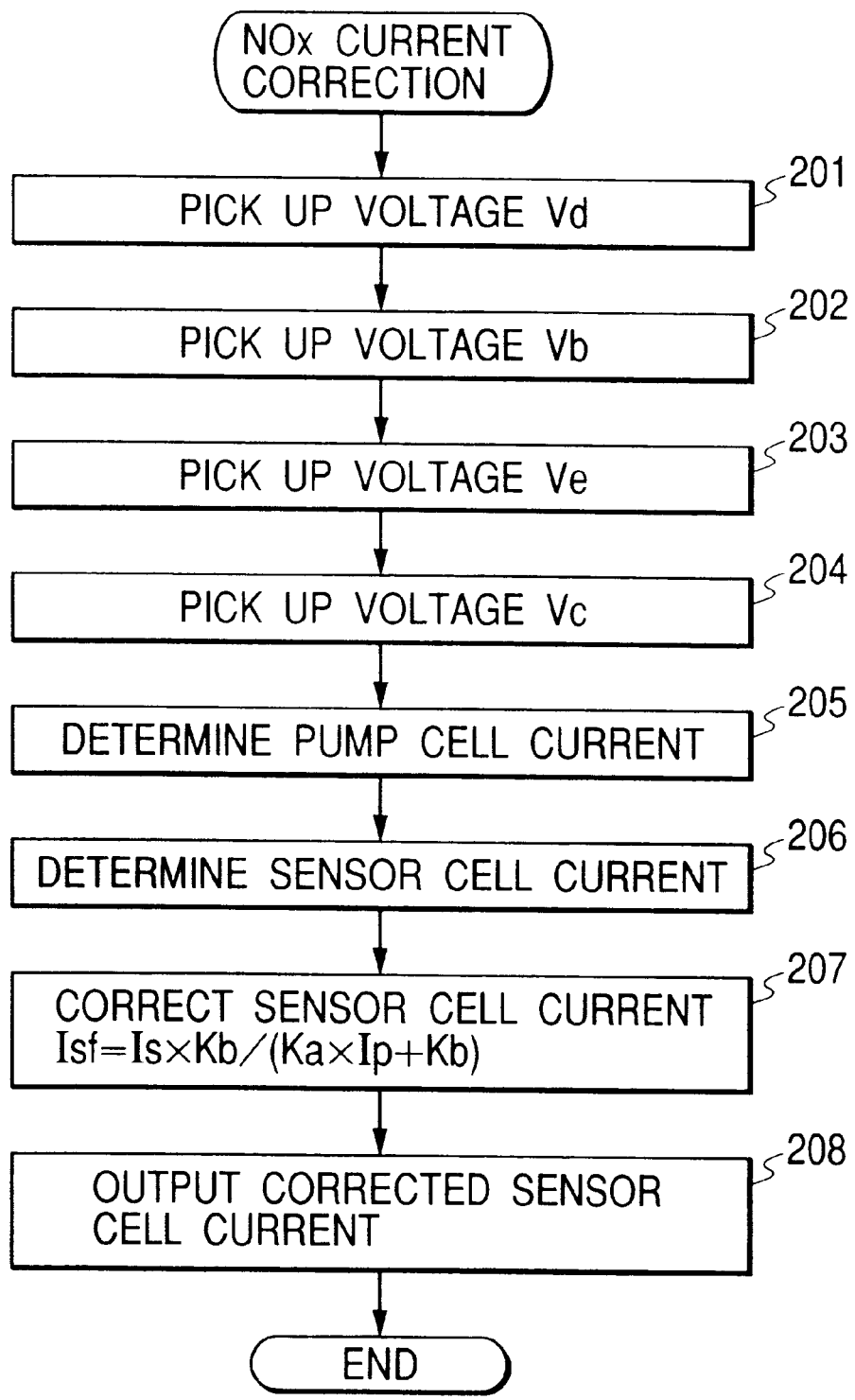
FIG. 10 is a flowchart of a program performed to correct a NOx current that is an output of a sensor cell.

FIG. 10 shows a NOx current correction subroutine performed by the CPU installed in the microcomputer shown in FIG. 8.

First, in step 201, the CPU picks up the voltage Vd which is developed at the terminal Vd (i.e., one end of the resistor 213) and converted into a digital signal through the A/D converter A/D11. Similarly, in steps 202, 203, and 204, the CPU picks up the voltages Vb, Ve, and Vc which are developed at the terminals Vb, Ve, and Vc and converted into digital signals through the A/D converters A/D12 to A/D14, respectively.

After step 204, the routine proceeds to step 205 wherein the pump cell current Ip (=(Vd−Vb)/R1) is determined. The routine proceeds to step 206 wherein the sensor cell current Is (=(Ve−Vc)/R2) is determined.

The routine proceeds to step 207 wherein the sensor cell current Is is corrected according to the equation (1) below using the pump cell current Is, a structural constant Ka defined directly by the structure of the gas concentration sensor 100, and a correction coefficient Kb defined by the sensitivity of the sensor cell 120 (i.e., the sensitivity to NOx when the concentration of $O_2$ is 0%) to produce the corrected sensor cell current Isf.

$$Isf = Is \cdot Kb / (Ka \cdot Ip + Kb) \quad (1)$$

where the structural constant Ka is determined by a diffusion coefficient, shape, and volume of a diffused resistor (i.e., the porous diffused layer 101), and positions of the electrodes of the pump cell 110 and the sensor cell 120.

Figure 33:
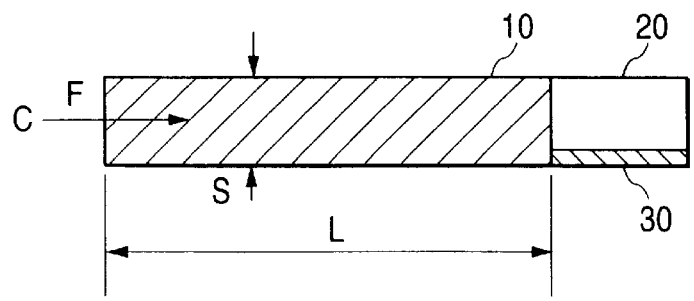
FIG. 33 is a sectional view which shows a sensor model used in explaining a method of finding a structural constant used in correcting a NOx current.

A method of determining the structural constant Ka will be discussed with reference to a simple sensor model shown in FIG. 33.

The sensor model includes a diffused resistor 10, a chamber 20, and an electrode 30. The diffused resistor 10 has a constant sectional area S and a length L. Assuming that a gas (NOx) having a concentration of C flows from left to right, as viewed in the drawing, that is, that NOx flows from a left surface of the diffused resistor 10 into the chamber 20 and reaches the electrode 30, the flow rate F of the gas is $$F = S \cdot C / L \cdot \alpha$$

where $\alpha$ is a diffused coefficient.

If the diffused resistor is made of a porous material or has formed therein a pin hole, the right side of the above equation is further multiplied by a given coefficient. Based on the thus calculated structural coefficient Ka, the flow rate F is determined.

In this embodiment, the structural constant Ka is determined as $$Ka = 1.95 \times 10^{-2}$$

For example, when the concentration of NOx is 1000 ppm, the sensor cell current Is is 8.13 $\mu$A. In this case, the correction coefficient Kb is $$Kb = 8.13 \times 10^{-3} (A)$$

For example, when the pump cell current Ip is 25 mA, the corrected sensor cell current Isf is obtained from the equation (1) as $$Isf = Is \cdot 8.13 \times 10^{-3} / (1.95 \times 10^{-2} \cdot 25 \times 10^{-3} + 8.13 \times 10^{-3}) = Is \cdot 0.943$$

It is found that the oxygen-caused error component that is equivalent to 6% of the sensor cell current Is is cancelled.

After the corrected sensor cell current Isf is determined, the routine proceeds to step 208 wherein the corrected sensor cell current Isf is outputted as the signal SG3, after which the routine terminates.

The output current (i.e., the sensor cell current Is) picked up directly from the sensor cell 120, indicating the concentration of NOx increases, as shown in FIG. 11(a), with an increase in concentration of $O_2$ reaching the sensor cell 120 without being decomposed by the pump cell 110. On the other hand, the output current (i.e., the corrected sensor cell current Isf) compensated for the oxygen-caused error component, as shown in FIG. 11(b), changes in proportion to a change in concentration of NOx.

Specifically, when $O_2$ contained in the exhaust gasses entering the porous diffused layer 101 is decomposed and discharged from the pump cell 110, it will cause the pressure in the porous diffused layer 101 to be decreased, sucking the NOx containing exhaust gasses flowing outside the pump cell 110. This excess of the exhaust gasses flows to the sensor cell 120 and contributes to an error component (i.e., the oxygen-caused error component) contained in the sensor cell current Is. The oxygen-caused error component is, however, eliminated by correcting the sensor cell current Is using the pump cell current Ip in the manner as discussed above to produce the corrected sensor cell current Isf indicating the concentration of NOx contained in the exhaust gasses accurately regardless of the concentration of oxygen.

Figure 12:
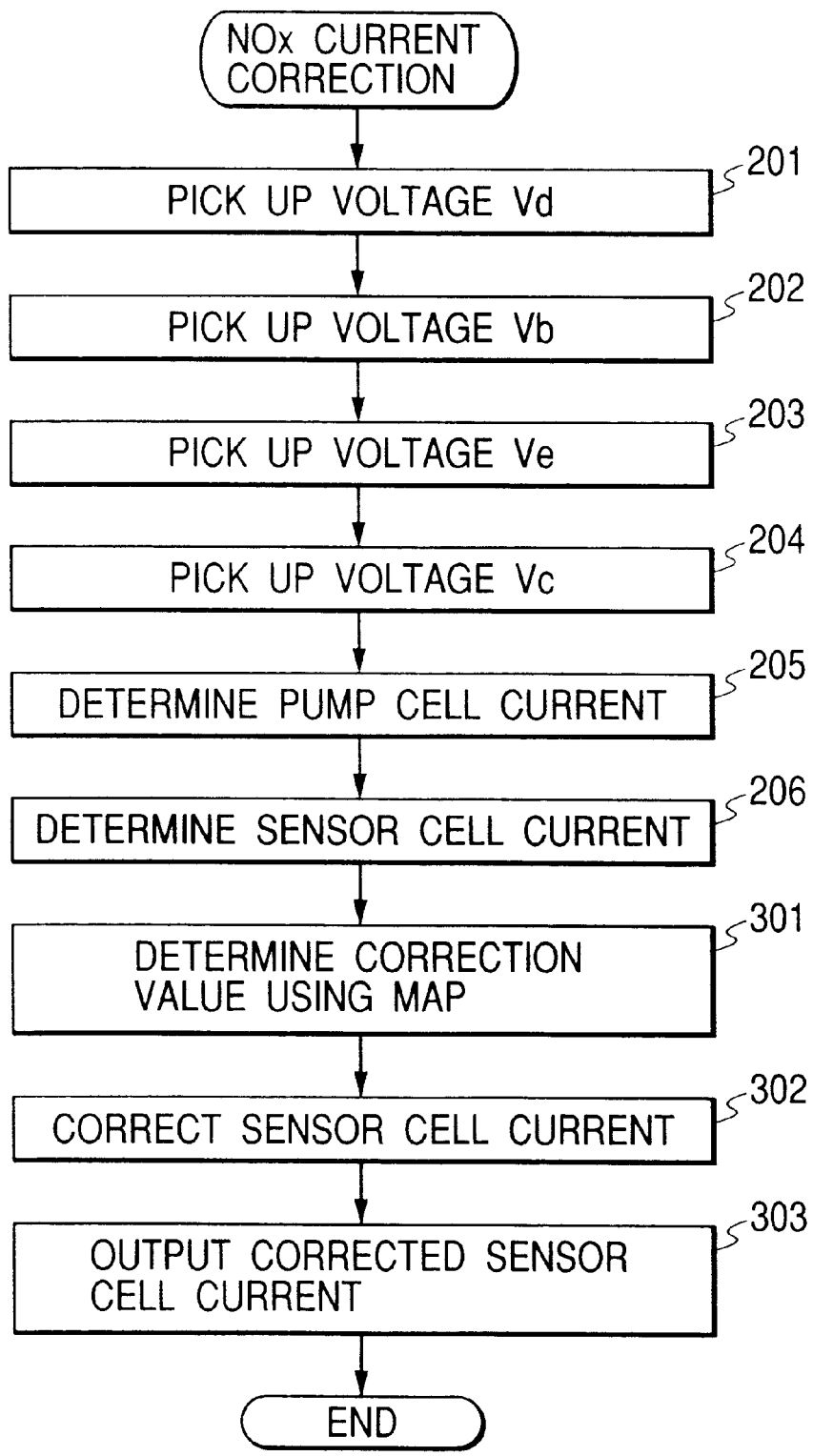
FIG. 12 is a flowchart of a program performed to correct a NOx current that is an output of a sensor cell according to the second embodiment of the invention.

FIG. 12 shows a NOx current correction subroutine according to the second embodiment of the invention. The same step numbers as employed in FIG. 10 refer to the same operations, and explanation thereof in detail will be omitted here.

Figure 13:
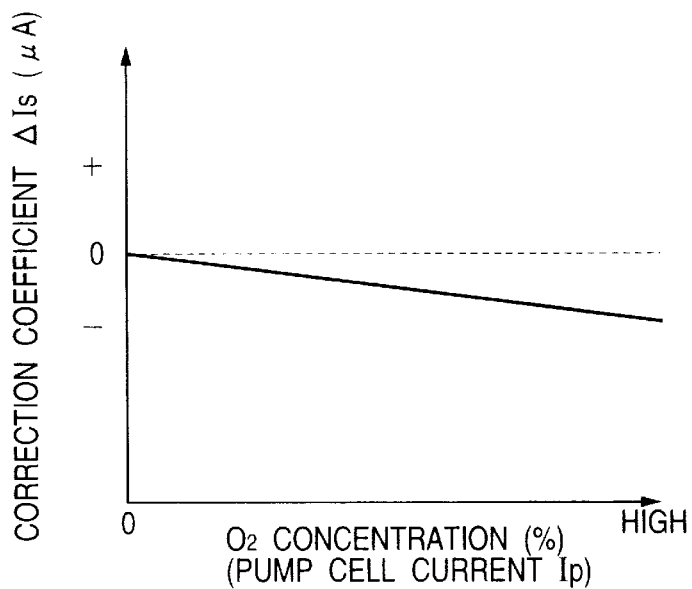
FIG. 13 is a map representing a relation between the concentration of oxygen and a correction value.

After the pump cell current Ip and the sensor cell current Is are determined through steps 210 to 206, the routine proceeds to step 301 wherein a correction value ΔIs is determined by look-up using a map, as shown in FIG. 13 as a function of the pump cell current Ip. The correction value ΔIs is decreased from zero (0) as the concentration of $O_2$ indicated by the pump cell current Ip increases. The mapped data in FIG. 13 may be derived based on the equation (1) as described above.

The routine proceeds to step 302 wherein the correction value ΔIs is added to the sensor cell current Is to produce the corrected sensor cell current Isf(=Is+ΔIs). The routine proceeds to step 303 wherein the corrected sensor cell current Isf is outputted as the signal SG3, after which the routine terminates.

Figure 14:
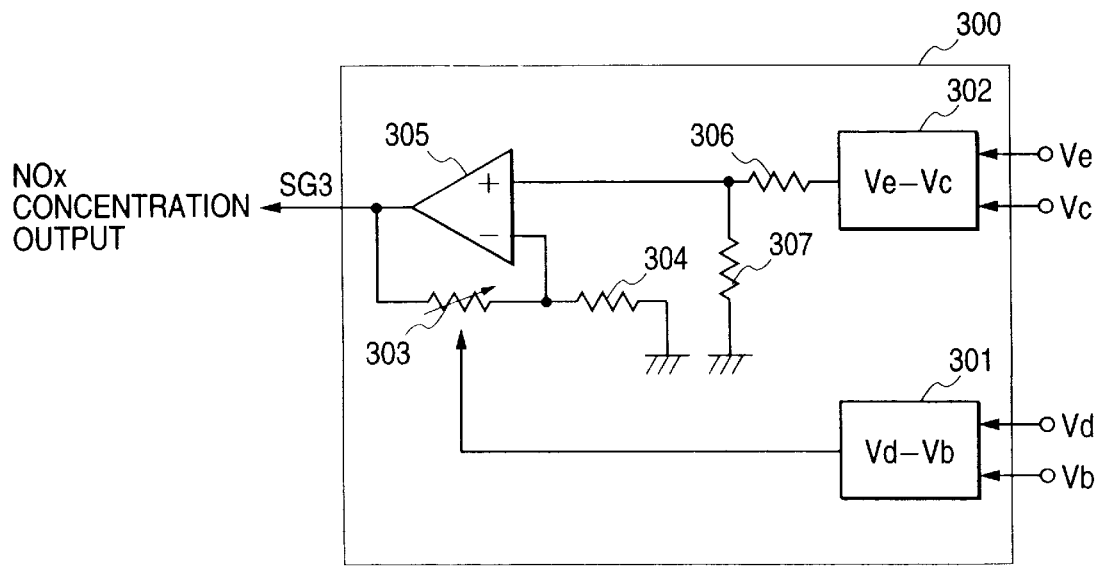
FIG. 14 is a circuit diagram which shows a NOx current correction circuit according to the third embodiment of the invention.

FIG. 14 shows an internal structure of the NOx current correction circuit 300 according to the third embodiment of the invention which may be employed instead of the one shown in FIG. 8.

The NOx current correction circuit 300 includes a pump cell current-to-voltage converting circuit 301, a sensor cell current-to-voltage converting circuit 302, a variable resistor 303, a resistor 304, an amplifier 305, and resistors 306 and 307 disposed between the sensor cell current-to-voltage converting circuit 302 and the amplifier 305.

The pump cell current-to-voltage converting circuit 301 receives the voltages Vd and Vb developed at the terminals Vd and Vb, as shown in FIG. 2, and outputs a voltage (Vd−Vb) corresponding to the pump cell current Ip. The variable resistor 303 is responsive to the voltage outputted from the pump sensor current-to-voltage converting circuit 301 to set a resistance value thereof The sum of the resistance values of the variable resistor 303 and the resistor 304 determines the amplification factor of the amplifier 35 as used as a correction coefficient for the sensor cell current Is for compensating for the above described oxygen-caused error component. The greater the pump cell current Ip, the smaller the resistance value of the variable resistor 303, thereby causing the amplification factor of the amplifier 305 to be decreased.

The sensor cell current-to-voltage converting circuit 302 receives the voltages Ve and Vc developed at the terminals Ve and Vc, as shown in FIG. 2, and produces a voltage (Ve−Vc) corresponding to the sensor cell current Is. The voltage is then inputted to a non-inverting input of the amplifier 305 through a junction of the resistors 306 and 307 and amplified, or corrected according to the amplification factor determined as a function of the pump cell current Ip, after which it is outputted as the signal SG3.

The shown physical structure of the NOx current correction circuit 300 allows the SG3 signal indicative of the concentration of NOx continuously as compared with the first and second embodiments in which the SG3 signal is provided cyclically each time the subroutines in FIGS. 10 and 12 are executed.

Figure 21:
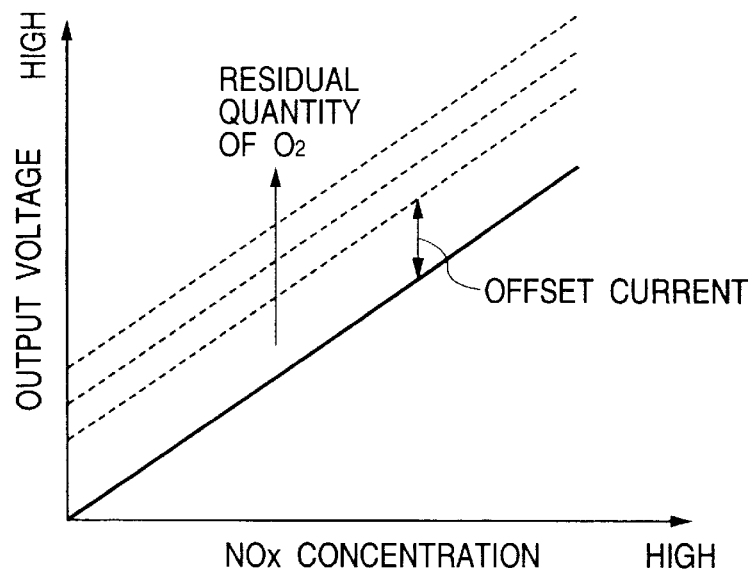
FIG. 21 is a graph which shows a relation between an output current of a sensor cell and the concentration of NOx.

The part of $O_2$ contained in the exhaust gasses entering the porous diffused layer 101 of the gas concentration sensor 100 is, as already described, left without being discharged from the pump cell 110, so that the sum of a current produced by NOx and the offset current produced by the residual $O_2$ flows through the sensor cell 120. The offset current has a value, as indicated by the lowermost curved line in FIG. 6, and is not produced if there is no residual $O_2$ in the porous diffused layer 101. The residual quantity of $O_2$ is, however, different among individual gas concentration sensors and changes as a function of deterioration of the gas concentration sensor, thus causing the offset current to be changed, as shown in FIG. 21, to change an error component in the sensor cell current Is.

Figure 15:
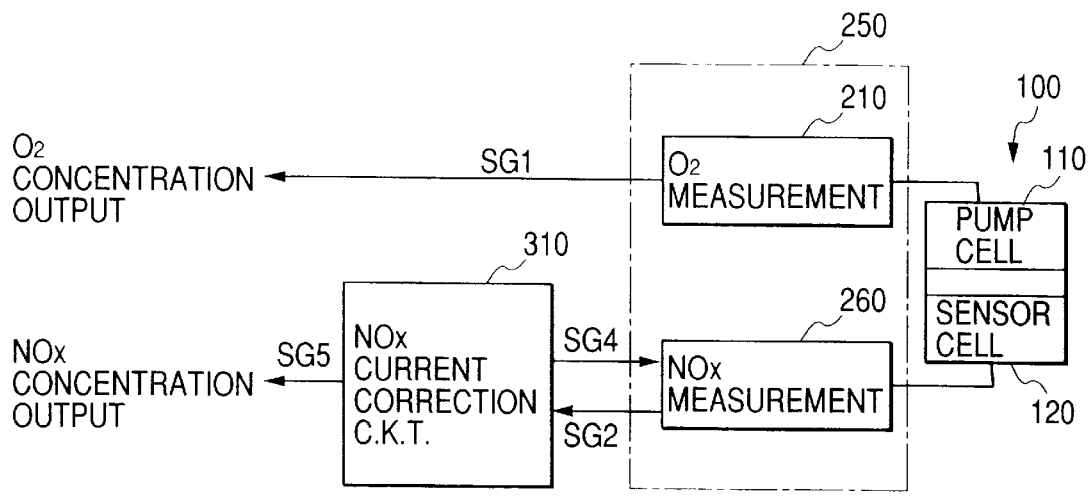
FIG. 15 is a block diagram which shows a gas concentration measuring apparatus according to the fourth embodiment of the invention.

FIG. 15 shows a gas concentration measuring apparatus according to the fourth embodiment of the invention which is designed to alleviate the above problem associated with the offset current. The same reference numbers as employed in the above embodiments refer to the same parts, and explanation thereof in detail will be omitted here.

The gas concentration measuring apparatus includes a sensor controller 250 and a NOx current correction circuit 310. The sensor controller 250 includes an oxygen concentration determining circuit 210 and a NOx concentration determining circuit 260. The oxygen concentration determining circuit 210, like the one shown in FIG. 1, provides the SG1 signal indicative of the concentration of $O_2$.

The NOx concentration determining circuit 260 not only provides the SG2 signal indicative of the concentration of NOx, but also controls the voltage applied to the sensor cell 120 in response to a signal SG4, as will be described later in detail, outputted from the NOx current correction circuit 310.

The NOx current correction circuit 310 measures the offset current produced as a function of the quantity of $O_2$ remaining without being discharged by the pump cell 110 and compensates for an error component of the NOx current (i.e., the sensor cell current Is) produced by the offset current to provide the signal SG5 indicative of the error-corrected NOx current.

In order to measure the offset current directly from the gas concentration sensor 100 which changes as a function of the residual quantity of $O_2$, the gas concentration sensor has the following modified structure.

In the gas concentration sensor 100 shown in FIG. 3, the first pump cell electrode 111, the first sensor cell electrode 121, and the second sensor cell electrode 122 are each made of a noble metal with a high catalytic activity such as platinum, while the second pump electrode 112 is made of a noble metal such as Au—Pt which hardly decomposes NOx. The second pump cell electrode 112, however, has the feature, as described above in FIG. 5, that if the voltage applied to the pump cell 110 exceeds a certain upper limit, it will cause the NOx molecules to be decomposed, thereby producing an additional current, as indicated by the broken curved line on each of the solid curved lines. In view of this phenomenon, the first sensor cell electrode 121 of the fourth embodiment is made of a noble metal such as Au-Pt in order to discriminate between a residual $O_2$-produced current and a NOx-produced current.

Figure 16:
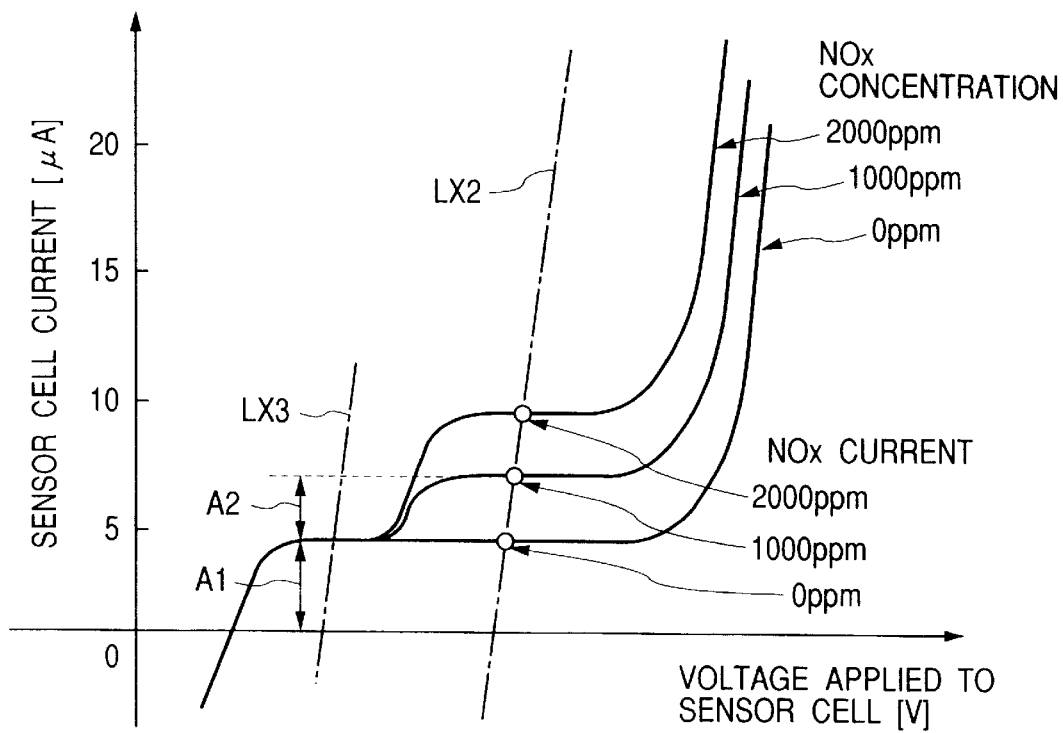
FIG. 16 is a graph which shows a relation between a sensor cell current flowing through a sensor cell and a voltage applied to the sensor cell.

Specifically, the first pump cell electrode 111 of the pump cell 110 and the second sensor cell electrode 122 of the sensor cell 120 are each made of a noble metal such as platinum with a high catalytic activity, while the second pump cell electrode 112 and the first sensor cell electrode 121 are each made of a noble metal such as Au-Pt which hardly decomposes the NOx gas. This causes the sensor cell 120 to exhibit sensor cell current output characteristics, as shown in FIG. 16, in terms of the voltage applied to the sensor cell 120. Specifically, application of the voltage to the sensor cell 120 around the input voltage line LX2 causes the residual $O_2$-produced current (i.e., the offset current), as indicated by A1, and the NOx-produced current, as indicated by A2 to be contained in the sensor cell current Is. The application of the voltage to the sensor cell 120 along a broken line LX3 which is lower in voltage level than the line LX2 causes only the residual $O_2$-produced current (i.e., the offset current), as indicated by A1, to be contained in the sensor cell current Is.

Therefore, selective control of the voltage applied to the sensor cell 120 along one of the input voltage lines LX2 and LX3 enables the residual $O_2$-produced current (i.e., the offset current) and the NOx-produced current to be discriminated from each other.

Figure 17:
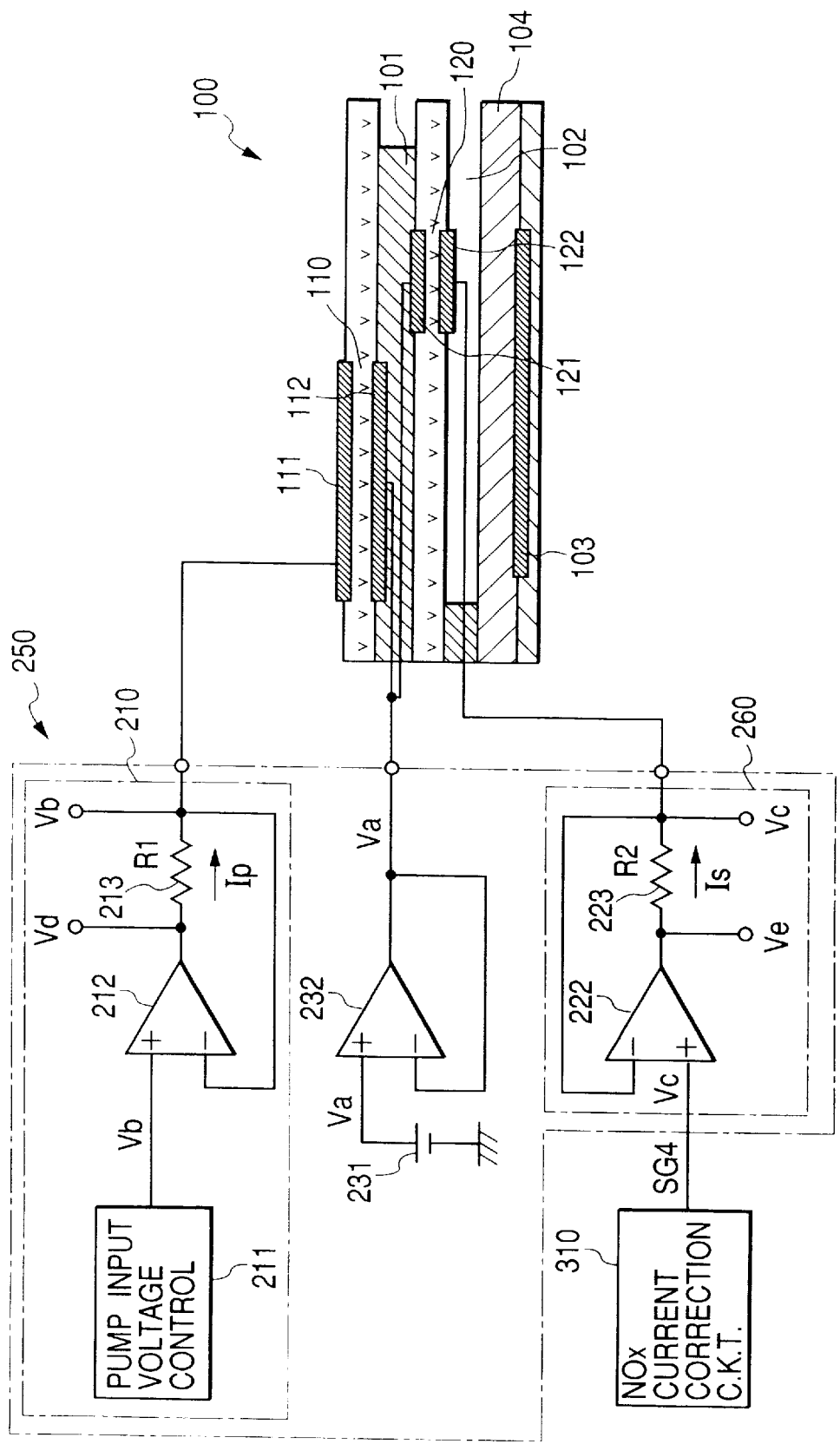
FIG. 17 is an illustration which shows structures of a gas concentration sensor and a sensor controller.

FIG. 17 shows an internal structure of the sensor controller 250 in FIG. 15 which is different from the one shown in FIG. 2 only in that the NOx current correction circuit 310 is connected directly to the non-inverting input of the amplifier 222. Other arrangements are identical, and explanation thereof in detail will be omitted here.

Figure 18:
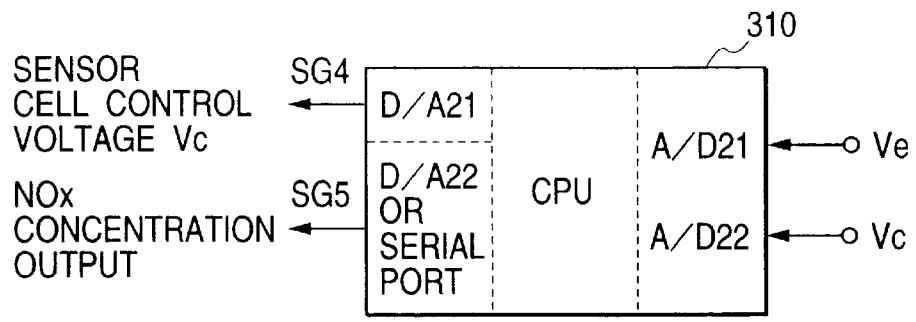
FIG. 18 is an illustration of a structure of a NOx current correction circuit.

The NOx current correction circuit 310 is, as shown in FIG. 18, made of a microcomputer consisting of a CPU, two D/A converters D/A21 and D/A22, and two A/D converters A/D21 to A/D22. The A/D converters A/D21 and A/D22 are connected to the terminals Ve and Vc, as shown in FIG. 17, respectively. The CPU determines the sensor cell current Is based on the voltages appearing at the terminals Ve and Vc (i.e., the signal SG2) and outputs an input control voltage Vc (i.e., the signal SG4) to the amplifiers 222 through the D/A converter D/A21 for controlling the voltage to be applied to the sensor cell 120. The CPU also determines the offset current produced by the residual $O_2$ based on the sensor cell current Is derived when the voltage is applied to the sensor cell 120 along the input voltage line LX3 in FIG. 16 and compensates for an error component of the sensor cell current Is caused by the offset current to produce the signal SG5 indicative of the offset current-compensated sensor cell current Is. The signal SG5 is outputted through the D/A converter D/A22 or a serial output port.

Figure 19:
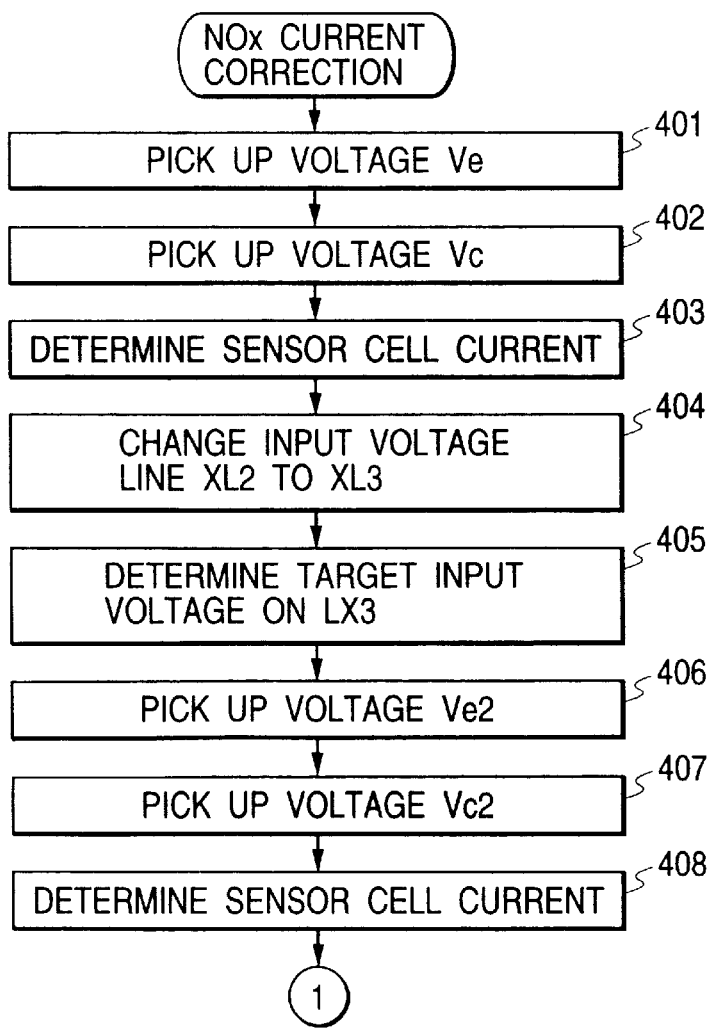
FIGS. 19 and 20 show a flowchart of a program performed to correct a NOx current that is an output of a sensor cell according to the fourth embodiment of the invention.
Figure 20:
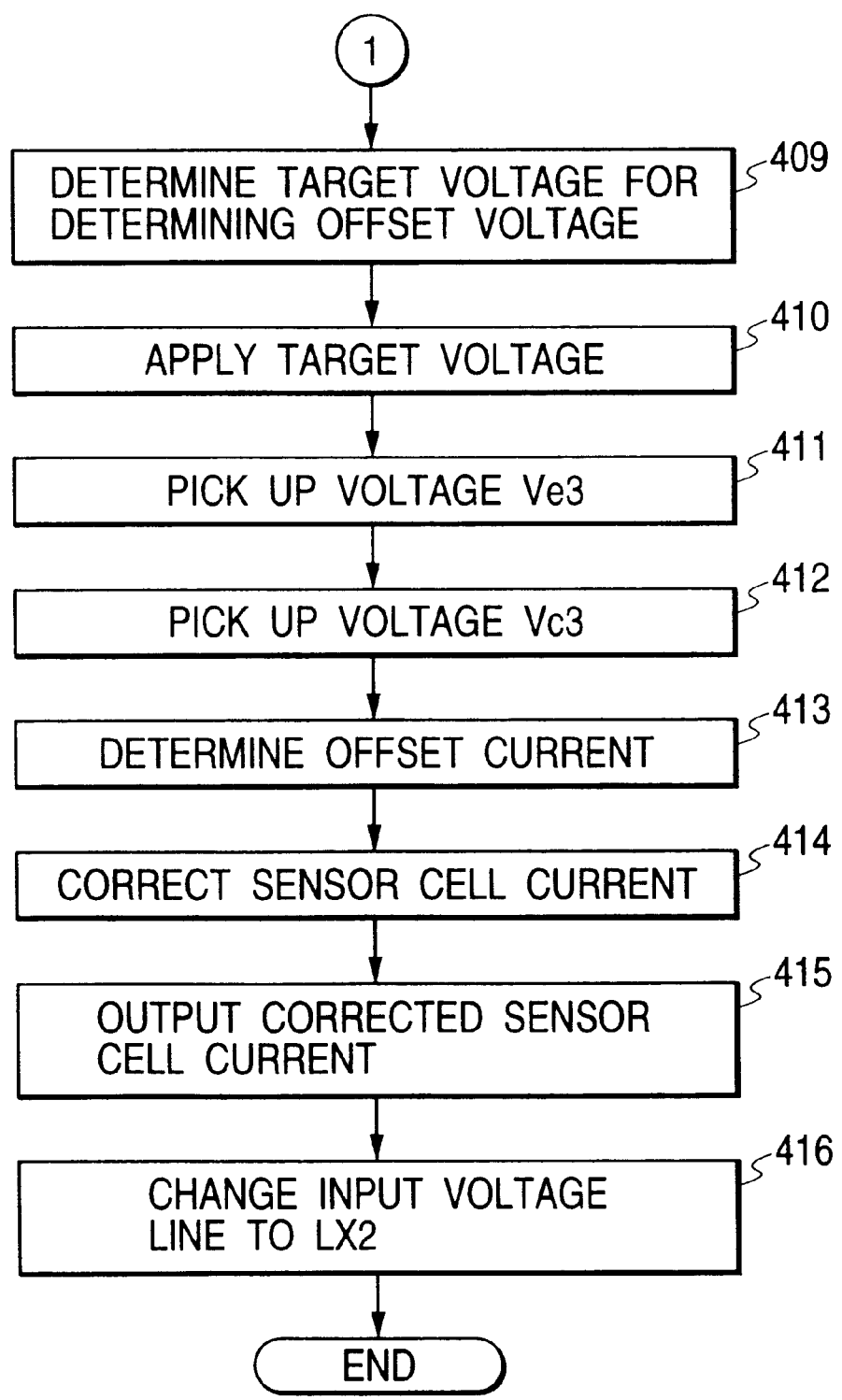

FIGS. 19 and 20 show a NOx current correction subroutine performed by the CPU installed in the microcomputer shown in FIG. 18.

First, in step 401, the CPU picks up the voltage Ve which is developed at the terminal Ve and converted into a digital signal through the A/D converter A/D21. Similarly, in step 402 the CPU picks up the voltage Vc which is developed at the terminal Vc and converted into a digital signal through the A/D converters A/D22.

The routine proceeds to step 403 wherein the sensor cell current Is (=(Ve−Vc)/R2) is determined. The routine proceeds to step 404 wherein the input voltage line LX2 used to determine the voltage to be inputted to the sensor cell 120 is changed to LX3. The routine proceeds to step 405 wherein a given one of x coordinates of the input voltage line LX3 in FIG. 16 is selected as a target input voltage and then applied to the sensor cell 120 Specifically, the NOx current correction circuit 310 outputs the signal SG4 indicative of the selected input control voltage Vc to the amplifiers 222 of the sensor controller 250.

After a lapse of a given period of time (e.g., several tens to two hundred ms), the routine proceeds to steps 406 and 407 wherein the CPU picks up the voltages developed at both ends of the resistor 223 (i.e., the terminals Ve and Vc) through the A/D converters A/D21 and A/D22, which will be referred to as voltages Ve2 and Vc2 below.

The routine proceeds to step 408 wherein a sensor cell current Is2 is determined using the voltages Ve2 and Vc2 derived in steps 406 and 407 (Is2=(Ve2−Vc2)/R2).

The routine proceeds to step 409 in FIG. 20 wherein a target input voltage to be applied to the sensor cell 120 is selected from the input voltage line LX3 which corresponds to the sensor cell current Is2 determined in step 408. The routine proceeds to step 410 wherein the target input voltage selected in step 409 is inputted as the input control voltage Vc to the amplifier 222 of the NOx concentration determining circuit 260 through the D/A converter D/A21.

After a lapse of a given period of time (e.g., several tens to two hundred ms), the routine proceeds to step 411 and 412 wherein the CPU picks up the voltages developed at both ends of the resistor 223 (i.e., the terminals Ve and Vc) through the A/D converters A/D21 and A/D22, which will be referred to as voltages Ve3 and Vc3 below.

The routine proceeds to step 413 wherein a sensor cell current, that is, an offset current Iso is determined using the voltages Ve3 and Vc3 derived in steps 411 and 412 (Iso=(Ve3−Vc3)/R2).

The routine proceeds to step 414 wherein the offset current Iso is subtracted from the sensor cell current Is determined in step 403 to produce the corrected sensor cell current Isf(=Is−Iso).

The routine proceeds to step 415 wherein the corrected sensor cell current Isf is outputted as the signal SG5. The routine proceeds to step 416 wherein the input voltage line LX3 is returned to LX2, after which the routine terminates.

A change in the offset current Iso with a change in voltage applied to the sensor cell 120 is, as can be seen from FIG. 16, relatively small. Thus, the voltage to be applied to the sensor cell 120 for determining the offset current Iso may be set to a constant value. Specifically, the sensor cell current Is2 determined in step 408 may be used as the offset current Iso. This allows steps 409 to 413 to be emitted.

Figure 22:
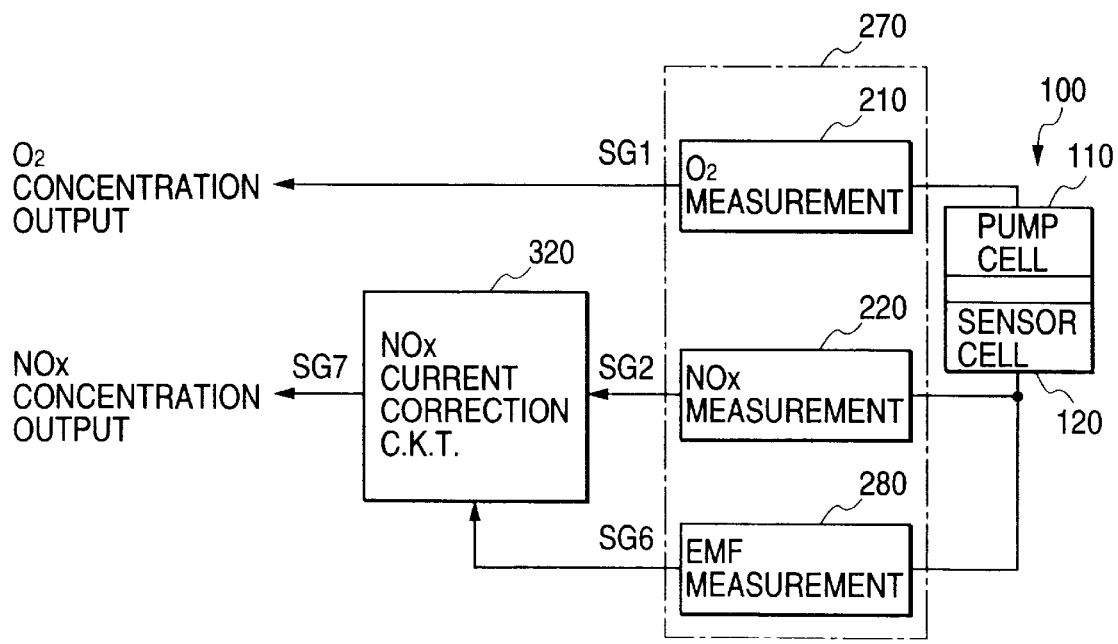
FIG. 22 is a block diagram which shows a gas concentration measuring apparatus according to the fifth embodiment of the invention.

FIG. 22 shows a gas concentration measuring apparatus according to the fifth embodiment of the invention which is a modification of the fourth embodiment and designed to measure an electromotive force produced by the sensor cell 120 that is changed as a function of the quantity of $O_2$ remaining on the sensor cell 120 for correcting the NOx current (i.e., the sensor cell current Is).

If there is no $O_2$ remaining on the sensor cell 120, the sensor cell 120 produces an electromotive force of approximately 0.45V indicating to the stoichiometric. Alternatively, if the residual quantity of $O_2$ increases, it will cause the electromotive force produced by the sensor cell 120 to decrease. Specifically, a change in quantity of $O_2$ remaining on the sensor cell 120 causes the electromotive force produced by the sensor cell 120 to be changed, thereby resulting in a change in NOx current outputted by the sensor cell 120, as shown in FIG. 26(a), regardless of an actual concentration of NOx. Using this fact, the fifth embodiment corrects the NOx current (i.e., the sensor cell current Is) to compensate for a residual $O_2$-caused error component.

The gas concentration measuring apparatus of this embodiment includes, as shown in FIG. 22, a sensor controller 270 and a NOx current correction circuit 320.

The sensor controller 270 includes an oxygen concentration determining circuit 210, a NOx concentration determining circuit 220, and an electromotive force determining circuit 280. The oxygen concentration determining circuit 210 and the NOx concentration determining circuit 220 are identical with the ones shown in FIG. 1, and explanation thereof in detail will be omitted here. The electromotive force determining circuit 280 measures the electromotive force produced by the sensor cell 120 and outputs a signal SG6 indicative thereof to the NOx current correction circuit 320.

The NOx current correction circuit 320 receives the signal SG6 indicative of the electromotive force produced by the sensor cell 120 and corrects the signal SG2 indicative of the concentration of NOx outputted from the NOx concentration determining circuit 220 to produce an error-corrected NOx current signal SG7.

Figure 23:
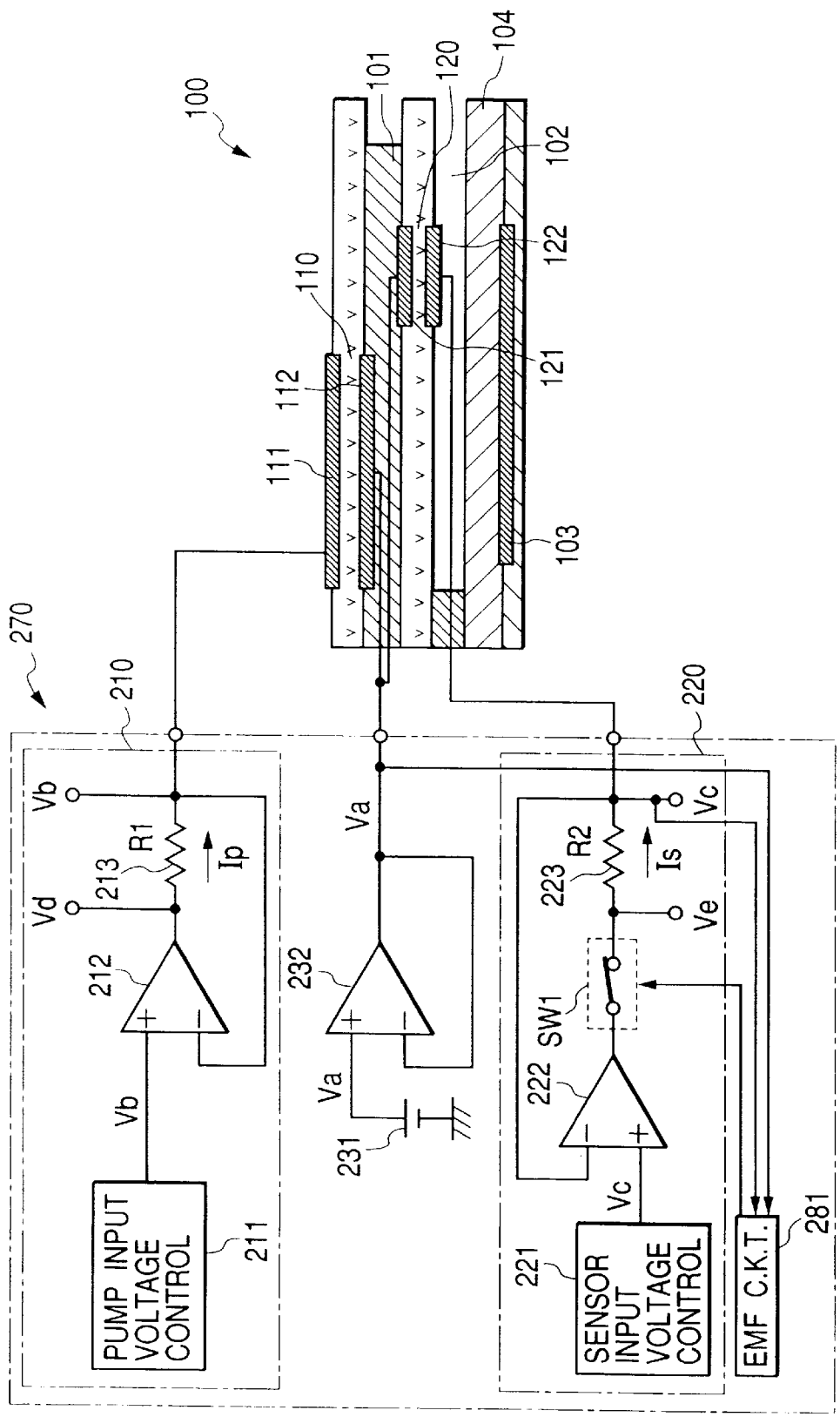
FIG. 23 is an illustration which shows structures of a gas concentration sensor and a sensor controller.

FIG. 23 shows an internal structure of the sensor controller 270 which is different from the one shown in FIG. 2 only in that a normally closed switch SW1 is disposed between the resistor 223 and the amplifier 222, and an electromotive force measuring circuit 281 is provided to selectively open and close the switch SW1 and to measure the electromotive force when the switch SW1 is opened. The electromotive force determining circuit 280 shown in FIG. 22 is made up of the switch SW1 and the electromotive force measuring circuit 281. Other arrangements of the sensor controller 270 and structure of the gas concentration sensor 100 are identical with the ones in the first embodiment, and explanation thereof in detail will be omitted here.

Figure 24:
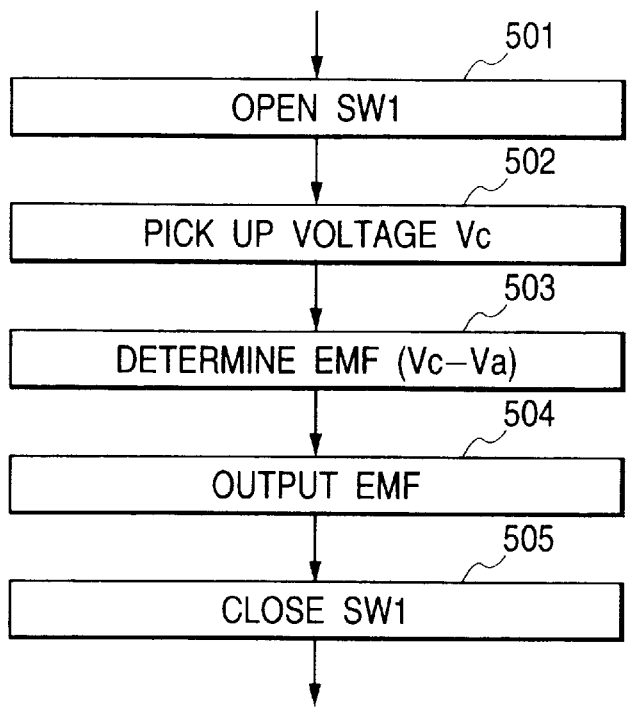
FIG. 24 is a flowchart of a program to control a switch for blocking and establishing communication between a sensor cell and a voltage applying circuit.
Figure 25:
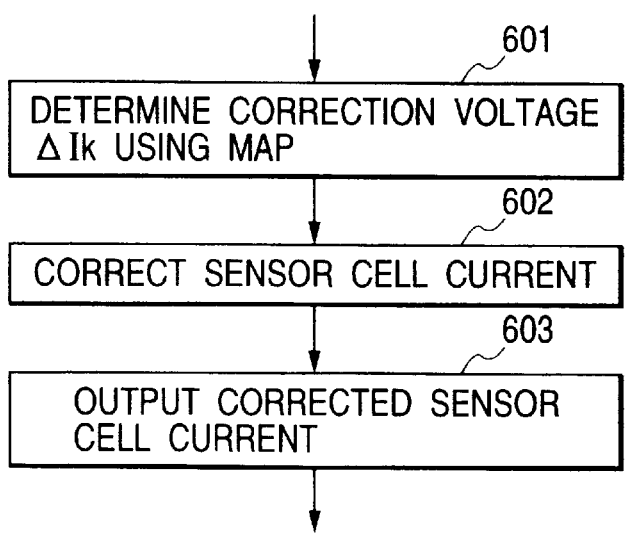
FIG. 25 is a flowchart of a program to correct a NOx current that is an output of a sensor cell.

FIGS. 24 and 25 show programs performed by the electromotive force measuring circuit 281 and the NOx current correction circuit 320, respectively.

After entering the program in FIG. 24, the routine proceeds to step 501 wherein a CPU built in the electromotive force measuring circuit 281 outputs an ON-signal to open the switch SW1 to block communication between the amplifier 222 and the resistor 223. The routine proceeds to step 502 wherein the voltage of the second sensor cell electrode 122, that is, the voltage Vc developed at the terminal Vc is picked up through an A/D converter. The routine proceeds to step 503 wherein the electromotive force (EMF) produced by the sensor cell 120 is determined using the voltage Vc derived in step 502 and the constant voltage Va developed at the first sensor cell electrode 121 (EMF=Vc−Va).

The routine proceeds to step 504 wherein the signal SG6 indicative of the electromotive force determined in step 503 is outputted to the NOx current correction circuit 320. The routine proceeds to step 505 wherein the switch SW1 is closed.

Upon input of the signal SG6 to the NOx current correction circuit 320, the program in FIG. 25 is initiated.

Figure 27:
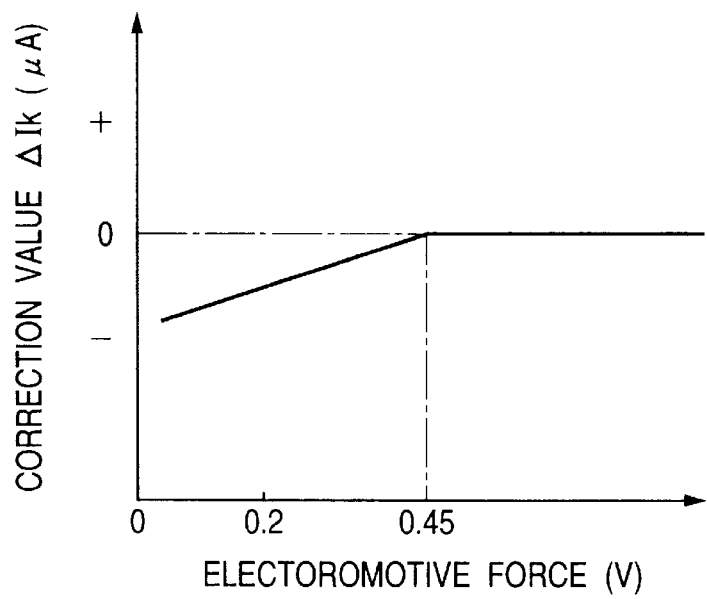
FIG. 27 is a map representing an electromotive force produced by a sensor cell and a correction value.

First, in step 601, a correction value ΔIk is determined by look-up using a map, as shown in FIG. 27, based on the electromotive force determined in step 503. The map is so prepared that the correction value ΔIk is decreased from zero (0) as the electromotive force is decreased from 4.5V indicating the stoichiometric for compensating for the residual $O_2$-caused error component contained in the sensor cell current Is provided by the NOx concentration determining circuit 220 so that an output of the NOx current correction circuit 320 may change, as shown in FIG. 26(b), in direct proportion to the concentration of NOx.

The routine proceeds to step 602 wherein the correction value ΔIk is added to the sensor cell current Is inputted from the NOx concentration determining circuit 220 to produce the corrected sensor cell current Isf(=Is+ΔIk) The routine proceeds to step 603 wherein the corrected sensor cell current Isf is outputted as the signal SG7 through a D/A converter or a serial output port, after which the routine terminates.

Figure 28:
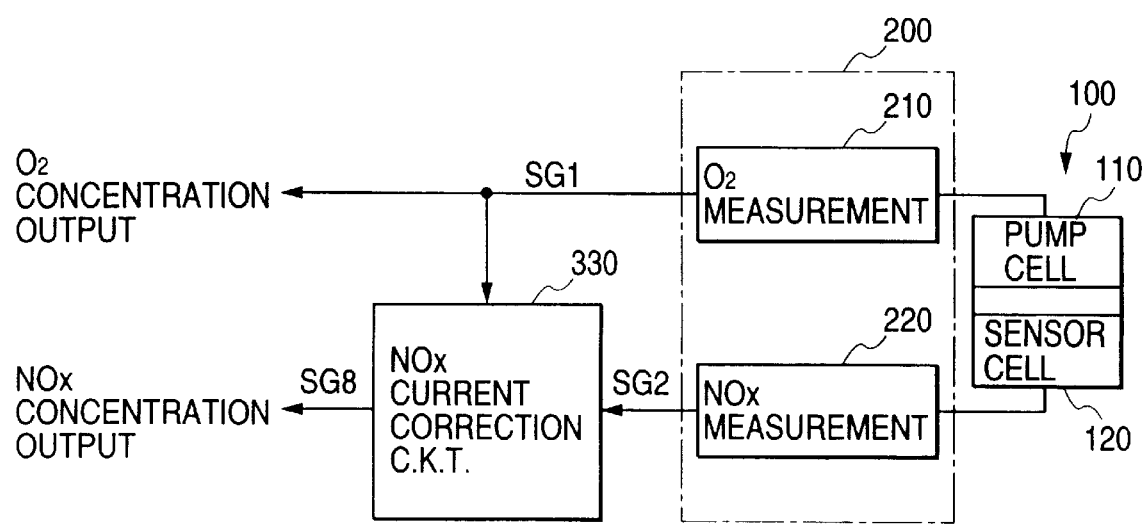
FIG. 28 is a block diagram which shows a gas concentration measuring apparatus according to the sixth embodiment of the invention.

FIG. 28 shows a gas concentration measuring apparatus according to the sixth embodiment of the invention which is designed to compensate both for the oxygen-caused error component, as compensated for by the first to third embodiments, and for the residual $O_2$-caused error component, as compensated for by the fourth and fifth embodiments.

The gas concentration measuring apparatus of this embodiment is different from the one shown in FIG. 1 only in that a NOx current correction circuit 330 is designed to provide a signal SG8 in the form of the NOx current whose oxygen-caused error component and residual $O_2$-caused error component are compensated for. Other arrangement are identical, and explanation thereof in detail will be omitted here.

The NOx current correction circuit 330 may be made by a combination of any one of the NOx current correction circuits 300 in the first to third embodiments and either of the NOx current correction circuits 310 and 320 in the fourth and fifth embodiments.

Figure 29:
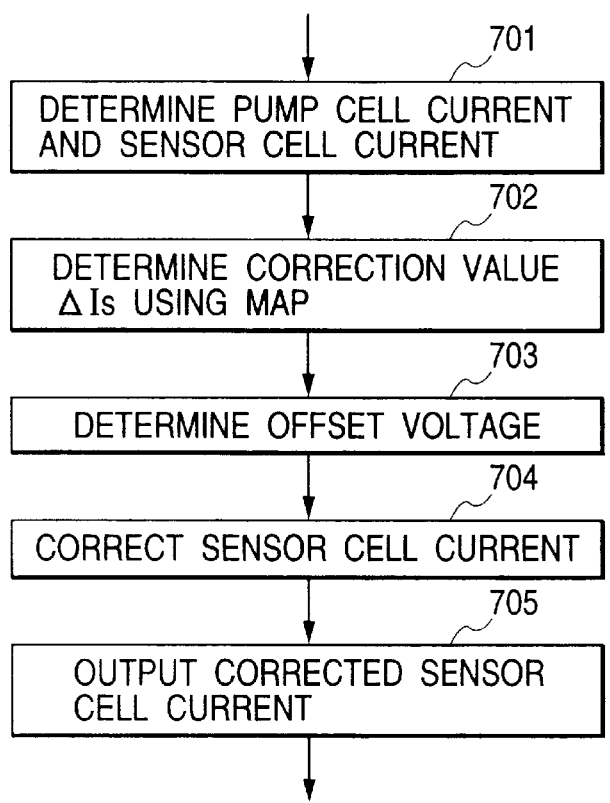
FIG. 29 is a flowchart of a program to correct a NOx current is an output of a sensor cell.

FIG. 29 shows, as one example, a program executed by the NOx current correction circuit 330 for producing the above described signal SG8.

After entering the program, the routine proceeds to step 701 wherein the pump cell current Ip and the sensor cell current Is are determined in the same manner as described in the above embodiments (e.g., steps 201 to 206 in FIG. 10). The routine proceeds to step 702 wherein the correction value ΔIs is determined based on the pump cell current Ip. The correction value ΔIs is used to correct the NOx current (i.e., the sensor cell current Is) for compensating the oxygen-caused error component and may be determined, like step 301 in FIG. 12, by look-up using the map shown in FIG. 13.

The routine proceeds to step 703 wherein the offset current Iso is determined which changes as a function of the quantity of $O_2$ remaining near the sensor cell 120. The offset current Iso may be determined in the same manner as in steps 401 to 413 of FIGS. 19 and 20. The second pump cell electrode 112 and the first sensor cell electrode 121 of the gas concentration sensor 100, however, need to be made of a metal such as Au—Pt which hardly decomposes NOx for measuring the offset current directly which depends upon the residual quantity of $O_2$.

The routine proceeds to step 704 wherein the sensor cell current Is is corrected according to an equation below to produce the corrected sensor cell current Isf.

$$Isf=Is+\Delta Is-Iso$$

The routine proceeds to step 705 wherein the signal SG7 indicative of the corrected sensor cell current Isf is outputted through a D/A converter or a serial output port.

The correction of the sensor cell current Is may alternatively is achieved using the above described equation (1) of Isf=Is·Kb/(Ka·Ip+Kb). Specifically, in step 704, the corrected sensor cell current Isf is determined using the following equation:

$$Isf=(Is-Iso)\cdot Kb/(Ka\cdot Ip+Kb).$$

Further, elimination of the residual $O_2$-caused error component may also be achieved using the correction value ΔIk determined by look-up using the map shown in FIG. 27.

Possible modifications which may be included to the above described embodiments will be discussed below.
(First Modification)

Figure 30:
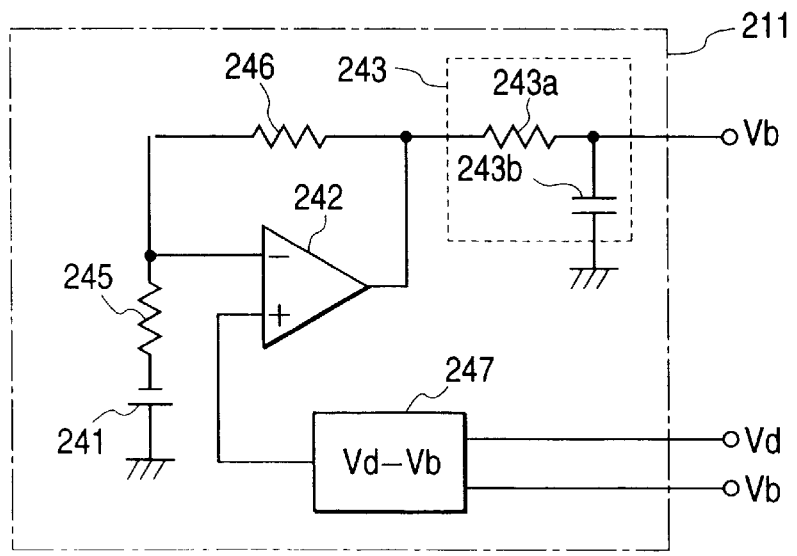
FIG. 30 is a circuit diagram which shows a sensor input voltage control circuit according to the first modification of the invention.

The pump input voltage control circuit 211 and the sensor input voltage control circuit 221 are each made up of components, as shown in FIG. 30. The circuits 211 and 221 have the same structure, and the following discussion will refer only to the structure of the pump input voltage control circuit 211 with reference to FIG. 30 for the brevity of disclosure.

The pump input voltage control circuit 211 includes a reference voltage circuit 241, an amplifier 242, amplifying resistors 245 and 246, a low-pass filter 243, and a current measuring circuit 247. The current measuring circuit 247 picks up the voltages Vd and Vb developed at both ends of the resistor 213 and provides a voltage difference (Vd−Vb) to a non-inverting input of the amplifier 242. The amplifier 242 connects at an inverting input to the resistors 245 and 246 for determining the amplification factor and at an output to the low-pass filter 243 for output of the input control voltage Vb. The low-pass filter 243 consists of a resistor 243a and a capacitor 243b.

The reference voltage circuit 241 generates an offset voltage on the input voltage line LX1 shown in FIG. 5 that is the voltage required to have the pump cell 110 output 0 mA. The amplifier 242 and the resistors 245 and 246 serve to define an inclination of the input voltage line LX1 (i.e., a ratio of an increase in input voltage to be applied to the pump cell 110 to an increase in output current of the pump cell 110). With this structure, the pump input voltage control circuit 211 applies the voltage to the pump cell 110 along the input voltage line LX1. Specifically, the voltage outputted from the pump input voltage control circuit 211 increases with an increase in pump cell current Ip under positive feedback control, so that the voltage will undergo oscillation, but the low-pass filter 243 installed in the feedback system serves to avoid such an oscillation.

(Second Modification)

The voltage at the common negative terminal of the pump cell 110 and the sensor cell 120 (i.e., the voltages developed at the second pump cell electrode 112 and the first sensor cell electrode 121) is, as described above, kept over the GND potential (i.e., 0V), but it may be connected directly to ground. Alternatively, the negative electrode of one of the pump cell 110 and the sensor cell 120 may be kept above 0V, while the negative electrode of the other cell may be connected to ground.

(Third Modification)

The gas concentration measuring apparatus of the sixth embodiment is designed to perform both the first sensor cell current correcting operation to compensate for the oxygen-caused error component which changes with a change in concentration of $O_2$ contained in gasses entering the gas concentration sensor 100 and the second sensor cell current correcting operation to compensate for the residual $O_2$-caused error component which changes with a deterioration and a unit-to-unit deviation of the gas concentration sensor 100. This modification is designed to perform the first and second sensor cell current correcting operations selectively as needed. For example, the second sensor cell current correcting operation is performed only when it is required to compensate for the residual $O_2$-caused error component. This may be achieved by performing a step after step 701 in FIG. 29 which determines whether the second sensor cell current correcting operation should be performed or not and performing step 702 only when it has been determined that the second sensor cell current correcting operation should be performed Alternatively, the number of times the second sensor cell current correcting operation is performed may be decreased as compared with the number of times the first sensor cell current correcting operation is performed. For example, the number of times the correction value ΔIs is determined using the map shown in FIG. 13 is set smaller than the number of times the offset current Iso is determined. This may be achieved by determining the correction value ΔIs at time intervals of several msec, while determining the offset current Iso at time intervals of several sec or alternatively determining the offset current Iso only when an ignition switch of the engine is turned on. In the case where the number of times the offset current Iso is determined is decreased, the determined offset current Iso may be stored in a backup memory, updated in a cycle, and read out of the memory only when the second sensor cell current correcting operation is performed.

(Fourth Modification)

The locations of the pump cell 110 and the sensor cell 120 of the gas concentration sensor 100 may be reversed. Specifically, the pump cell 110 is disposed between the porous diffused layer 101 and the air duct 102, while the sensor cell 120 is disposed on the porous diffused layer 101 so that it may be exposed to exhaust gasses flowing outside the gas concentration sensor 100. In order to provide the sensor cell characteristics shown in FIG. 6, only the electrode of the pump cell 110 exposed to the porous diffused layer 101 is made of a material which hardly decomposes NOx. Alternatively, in order to provide the sensor cell characteristics shown in FIG. 16, the electrodes of the pump cell 110 and the sensor cell 120 disposed on the side of the porous diffused layer 101 are made of a material which hardly decomposes NOx.

(Fifth Modification)

Figure 31:
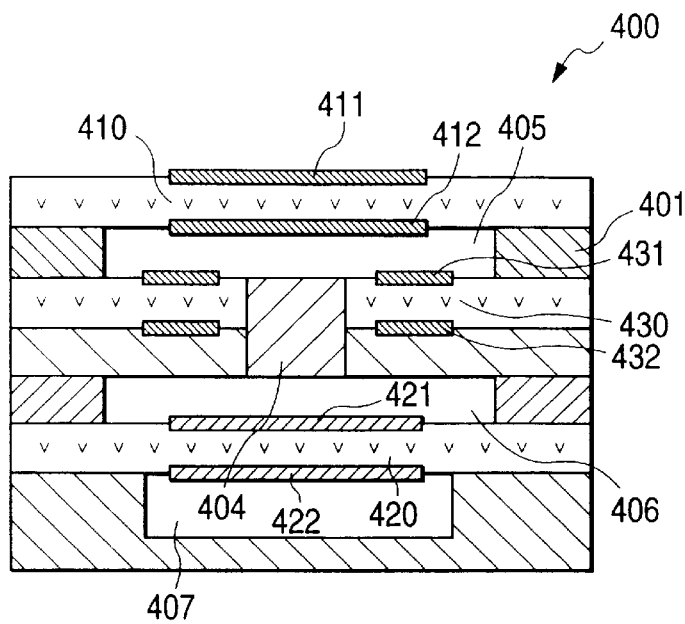
FIG. 31 is a sectional view which shows a structure of a three-cell gas concentration sensor used in the fifth modification of the invention.

The gas concentration sensor 100 may be made up of more than three cells. Additionally, each of the pump cell 110 and the sensor cell 120 may be formed with a plurality of cell segments. As one example, a three-cell gas concentration sensor is shown in FIG. 31.

The gas concentration sensor 400 includes a pump cell 410 which decomposes $O_2$ contained in exhaust gasses and discharges it to measure the concentration of $O_2$, a reference cell 430 which measures an oxygen pressure, and a sensor cell 420 which decomposes a NOx gas contained in the exhaust gasses and discharge oxygen ions thereof to measure the concentration of NOx.

The exhaust gasses of the engine flows into a first chamber 405 through a first porous diffused layer 401. The voltage at the reference cell 430, that is, the voltage appearing across a first reference cell electrode 431 and a second reference cell electrode 432 is monitored by, for example, the sensor controller 200. The sensor controller 200 controls the voltage applied to the first pump cell electrode 411 and the second pump cell electrode 412 based on the monitored voltage at the reference cell 430 so that the pump cell 410 may discharge only $O_2$ to the outside without decomposing NOx and measures the current flowing through the pump cell 410 to determine the concentration of $O_2$. After $O_2$ is discharged by the pump cell 410, the exhaust gasses enters a second chamber 406 through a second porous diffused layer 404. The sensor cell 420 decomposes the NOx gas contained in the exhaust gasses within the second chamber 406 and discharges oxygen ions thereof The sensor controller 200 measures the current flowing through the sensor cell 420 to determine the concentration of NOx contained in the exhaust gasses.

For example, when the exhaust gasses in the first chamber 405 are in a lean condition, that is, they contains much oxygen, it will cause the electromotive force produced at the reference cell 430 to be lowered, so that the voltage at the second reference cell electrode 432 drops. The pump cell 410 is controlled based on the electromotive force produced at the reference cell 430 to decompose and discharge $O_2$ to the outside, thereby causing the current (i.e., the pump cell current Is) to flow through the pump cell 410 as a function of the concentration of $O_2$ contained in the exhaust gasses. Alternatively, when the exhaust gasses in the first chamber 405 are in a rich condition, that is, they contains less oxygen, it will cause the electromotive force produced at the reference cell 430 to be increased, so that the voltage at the second reference cell electrode 432 is elevated. The pump cell 410 is controlled based on the electromotive force produced at the reference cell 430 to decompose and discharge $O_2$ to the outside, thereby causing the pump cell current Ip to flow through the pump cell 410 as a function of the concentration of $O_2$ contained in the exhaust gasses.

The application of the voltage to the sensor cell 420 will cause the NOx gas within the second chamber 406 to be ionized and discharged to the air duct 407, thereby causing the current (i.e., the sensor cell current Is) to flow through the sensor cell 420 as a function of the concentration of NOx contained in the exhaust gasses.

In order to compensate for the oxygen-caused error component depending upon the concentration of $O_2$ in the exhaust gasses entering the gas concentration sensor 400, the sensor cell current Is is corrected according to the relation below.

$$Isf = Is \cdot Kb / (Ka \cdot Ip + Kb)$$

where Ka is a structural constant determined by the structure of a diffused resistor consisting of the first and second porous diffused layers 401 and 404 and the first and second chambers 405 and 406, and Kb is a correction coefficient determined by the sensitivity of the sensor cell 420 to NOx. In practice, the structural constant Ka is defined by a diffusion coefficient, shape, and volume of the diffused resistor, and locations of the electrodes of the cells 410, 420, and 430.

In order to give the sensor cell characteristics shown in FIG. 16 to the gas concentration sensor 400 for compensating for the residual $O_2$-caused error component of the sensor cell current Is, the second pump cell electrode 412 and the first sensor cell electrode 421 are made of a material which hardly decomposes NOx.

(Sixth Embodiment)

Figure 32:
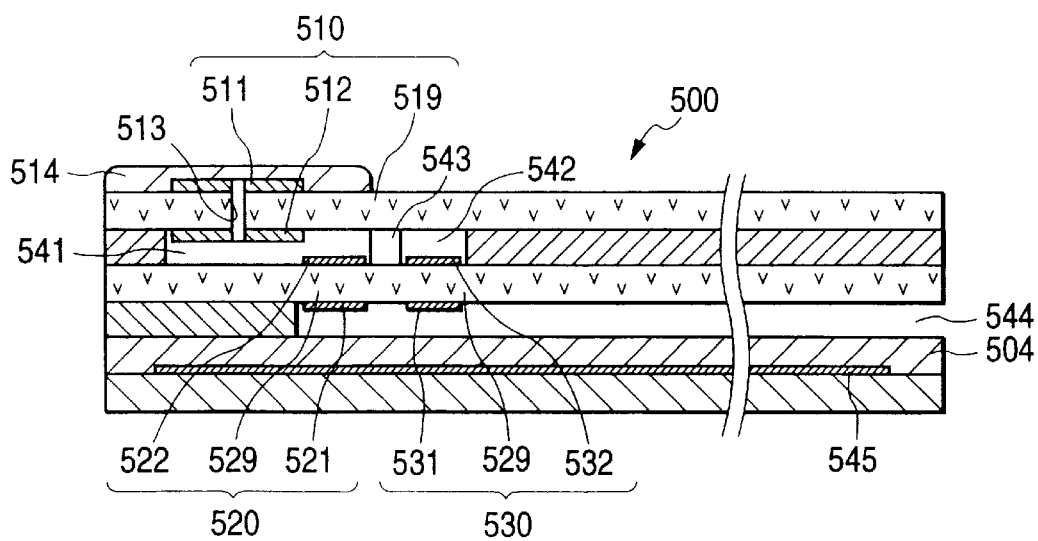
FIG. 32 is a sectional view which shows a structure of a three-cell gas concentration sensor used in the sixth modification of the invention.

FIG. 32 shows a three-cell gas concentration sensor of the type different from the one shown in FIG. 31.

The gas concentration sensor 500 includes an oxygen pump cell 510, an oxygen sensor cell 520, and a NOx sensor cell 530. The oxygen pump cell 510 consists of a solid electrolyte body 519 and a pair of electrodes 511 and 512 disposed on opposed surfaces of the solid electrolyte body 519. A pin hole 513 is formed through the solid electrolyte body 519 and the electrodes 511 and 512. A porous protective layer 514 is formed over the electrode 511.

The oxygen sensor cell 520 consists of a solid electrolyte body 529 and a pair of electrodes 521 and 522 disposed on opposed surfaces of the solid electrolyte body 529. The electrode 521 is made of, for example, a porous Pt. The electrode 522, like the electrode 512 of the oxygen pump cell 510, has an electrode activity adjusted to be inactive in reduction of NOx yet active in reduction of $O_2$.

The NOx sensor cell 530 consists of the solid electrolyte body 529 common to the oxygen sensor cell 520 and a pair of electrodes 531 and 532 disposed adjacent the electrodes 521 and 522, respectively. The electrode 531 is made of a porous Pt. The electrode 532 is made of a material such as a porous Pt which is active in reduction of NOx.

First and second chambers 541 and 542 are formed between the solid electrolyte bodies 519 and 529 in communication with each other through a hole 543. An air path 544 is formed between the solid electrolyte body 529 and an insulating layer 504 in communication with the atmosphere. A heater 545 is mounted in the insulating layer 504.

The exhaust gasses enters the first chamber 541 through the pin hole 513, which causes an electromotive force to be produced in the oxygen sensor cell 520 by a difference between concentrations of $O_2$ to which the electrodes 521 and 522 are exposed. The electromotive force is outputted to the sensor controller 200 as indicating the concentration of $O_2$ in the first chamber 541.

When the voltage is applied to the electrodes 511 and 512 of the oxygen pump cell 510, it will cause $O_2$ to be drawn into and discharged from the first chamber 541 so that the $O_2$ in the first chamber 541 is adjusted in concentration to a constant lower value. The power supply to the oxygen pump cell 510 is so adjusted under feedback control that the electromotive force generated across the electrodes 521 and 522 of the oxygen sensor cell 520 shows a given constant value. Since the electrode 512 of the oxygen sensor cells 520 within the first chamber 541 is, as described above, inactive in reduction of NOx, NOx in the first chamber 541 is not decomposed so that the quantity of NOx in the first chamber 541 is kept constant.

The exhaust gasses in which the concentration of $O_2$ is adjusted to the constant lower value by the oxygen pump cell 510 and the oxygen sensor cell 520 pass through the hole 543 and enter the second chamber 542. Since the electrode 532 of the NOx sensor cell 530 within the second chamber 542 is, as described above, active in reduction of NOx, application of voltage to the electrodes 531 and 532 of the NOx sensor cell 530 causes NOx on the electrode 532 to be decomposed, thereby causing an oxygen ion current (i.e., the sensor cell current Is) to flow through the electrode 532, which is, in turn, outputted to the sensor controller 200 as indicating the concentration of NOx.

In order to compensate for the oxygen-caused error component depending upon the concentration of $O_2$ in the exhaust gasses entering the gas concentration sensor 500, the sensor cell current Is is corrected according to the relation below.

$$Isf = Is \cdot Kb / (Ka \cdot Ip + Kb)$$

The structural constant Ka is determined by the structure of a diffused resistor consisting of the pin hole 513, the first and second chambers 541 and 542, and the hole 543. The correction coefficient Kb is determined by the sensitivity of the NOx sensor cell 530 to NOx. In practice, the structural constant Ka is defined by a diffusion coefficient, shape, and volume of the diffused resistor, and locations of the electrodes of the cells 510, 520, and 530.

In order to give the sensor cell characteristics shown in FIG. 16 to the gas concentration sensor 500 for compensating for the residual $O_2$-caused error component of the sensor cell current Is, the electrode 512 of the oxygen pump cell 510, the electrode 522 of the oxygen sensor cell 520, and the electrode 532 of the NOx sensor cell 530 are made of a material which hardly decomposes NOx.

(Seventh Embodiment)

A gas concentration sensor which is designed to decompose and discharge $O_2$ contained in gasses to be measured through a pump cell and decompose HC or CO contained in the gasses after the decomposition of $O_2$ through a sensor cell may be used in the above embodiments.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas concentration measuring apparatus comprising:

a gas concentration sensor including a diffused resistor into which gasses flow, a first cell responsive to application of a voltage to discharge oxygen contained in the gasses outside said gas concentration sensor, producing a first electric current as a function of concentration of the discharged oxygen, and a second cell responsive to application of a voltage to produce a second electric current as a function of concentration of a specified gas component contained in the gasses from which the oxygen is discharged by the first cell;

a first current measuring circuit measuring the first electric current flowing through the first cell of said gas concentration sensor;

a second current measuring circuit measuring the second electric current flowing through the second cell of said gas concentration sensor; and a correcting circuit correcting the second electric current measured by said second current measuring circuit based on the first electric current measured by said first current measuring circuit to compensate for an oxygen-caused error component of the second electric current which depends upon the concentration oxygen in the gasses and provide an error-corrected second electric current.

2. A gas concentration measuring apparatus as set forth in claim 1, wherein if the first electric current is defined as Ip and the second electric current is defined as Is, the correcting circuit provides the error-corrected second electric current Isf according to the following equation $$Isf = Is \cdot Kb/(Ka \cdot Ip + Kb)$$

where Ka is a structural constant defined by a structure of the gas concentration sensor, and Kb is a correction coefficient defined by sensitivity of the second cell.

3. A gas concentration measuring apparatus as set forth in claim 2, wherein the structural constant Ka is determined by a diffusion coefficient, a shape, and a volume of said diffused resistor, and locations of the first and second cell in the gas concentration sensor.

4. A gas concentration measuring apparatus as set forth in claim 1, wherein said correcting circuit stores correction data representing a relation between the concentration of oxygen in the gasses and the oxygen-caused error component of the second electric current and monitors the first electric current to determine the error-corrected second electric current based on the correction data.

5. A gas concentration measuring apparatus as set forth in claim 4, wherein the correction data is so defined that the concentration of the specified gas component indicated by the second electric -current is decreased as the concentration of oxygen indicated by the first electric current increases.

6. A gas concentration measuring apparatus comprising:

gas concentration sensor including a diffused resistor into which gasses flow, a first cell responsive to application of a voltage to discharge oxygen contained in the gasses outside said gas concentration sensor, producing a first electric current as a function of concentration of the discharged oxygen, and a second cell responsive to application of a voltage to produce a second electric current as a function of concentration of a specified gas component contained in the gasses from which the oxygen is discharged by the first cell; and a correcting circuit correcting the second electric current flowing through the second cell to compensate for a residual oxygen-caused error component contained in the second electric current which depends upon a quantity of oxygen remaining on the second cell without being discharged by the first cell.

7. A gas concentration measuring apparatus as set forth in claim 6, further comprising an offset current measuring circuit measuring an offset current flowing through the second cell as a function of the quantity of oxygen remaining on the second cell, and wherein said correcting circuit compensates for the residual oxygen-caused error component based on the offset current.

8. A gas concentration measuring apparatus as set forth in claim 7, wherein the second cell is so designed as to produce the offset current plus the second electric current in response to the application of the voltage in a first voltage level range and only the offset current in response to the application of the voltage in a second voltage level range different from the first voltage level range, and wherein said offset current measuring circuit applies the voltage within the second voltage level range to the second cell to measure the offset current.

9. A gas concentration measuring apparatus as set forth in claim 6, wherein the second cell is so designed as to produce the offset current plus the second electric current in response to the application of the voltage in a first voltage level range and only the offset current in response to the application of the voltage in a second voltage level range different from the first voltage level range, and wherein said correcting circuit applies the voltage within the first voltage level range to the second cell to measure the second electric current and applies the voltage within the second voltage level range to the second cell to measure the offset current, said correcting circuit compensating for the residual oxygen-caused error component based on the offset current.

10. A gas concentration measuring apparatus as set forth in claim 9, further comprising a switching circuit switching between a first and a second voltage application mode, in the first voltage application mode, the voltage in the first voltage level range being applied to the second cell, in the second voltage application mode, the voltage in the second voltage level range being applied to the second cell.

11. A gas concentration measuring apparatus as set forth in claim 6 further comprising an electromotive force measuring circuit measuring an electromotive force produced by the second cell as a function of the quantity of oxygen remaining on the second cell, and wherein said correcting circuit offsets the residual oxygen-caused error component of the second electric current based on the electromotive force measured by said electromotive force measuring circuit.

12. A gas concentration measuring apparatus as set forth in claim 11, wherein said electromotive force measuring circuit includes a switch which is turned on to block communication between the second cell of said gas concentration sensor and a voltage source applying the voltage to the second cell, said electromotive force measuring circuit measuring the electromotive force when the switch is turned on.

13. A gas concentration measuring apparatus comprising:

a gas concentration sensor including a diffused resistor into which gasses flow, a first cell responsive to application of a voltage to discharge oxygen contained in the gasses outside said gas concentration sensor, producing a first electric current as a function of concentration of the discharged oxygen, and a second cell responsive to application of a voltage to produce a second electric current as a function of concentration of a specified gas component contained in the gasses from which the oxygen is discharged by the first cell;

a first current measuring circuit measuring the first electric current flowing through the first cell of said gas concentration sensor;

a second current measuring circuit measuring the second electric current flowing through the second cell of said gas concentration sensor; and a correcting circuit performing a first correcting operation and a second correcting operation, the first correcting operation correcting the second electric current measured by said second current measuring circuit based on the first electric current measured by said first current measuring circuit to compensate for an oxygen-caused error component of the second electric current which depends upon the concentration of oxygen in the gasses, the second correcting operation correcting the second electric current to compensate for a residual oxygen-caused error component contained in the second electric current which depends upon a quantity of oxygen remaining on the second cell without being discharged by the first cell.

14. A gas concentration measuring apparatus as set forth in claim 13, wherein said correcting circuit selectively performing the first and second correcting operations according to given requirements of the first and second correcting operations.

15. A gas concentration measuring apparatus as set forth in claim 13, wherein said first and second current measuring circuits measure the first and second electric currents in a cycle, and wherein said correcting circuit performs the first correcting operation in a first cycle shorter than a second cycle in which the second correcting operation is performed.

16. A gas concentration sensor comprising:

a diffused resistor into which gasses flow;

a first cell responsive to application of a voltage to discharge oxygen contained in the gasses outside said gas concentration sensor, producing a first electric current as a function of concentration of the discharged oxygen; and a second cell responsive to application of a voltage to produce a second electric current as a function of concentration of a specified gas component contained in the gasses from which the oxygen is discharged by the first cell, the second cell being so designed as to produce an offset current plus the second electric current in response to the application of the voltage in a first voltage level range and only the offset current in response to the application of the voltage in a second voltage level range different from the first voltage level range.

17. A gas concentration sensor as set forth in claim 16, wherein each of the first and second cell includes a first electrode exposed to said diffused resistor and a second electrode located away from the diffused resistor, the first electrode of the first and second cells being made of a material which is inactive with respect to the specified gas component.

* * * * *

UNITED STATES PATENT AND TRADEMARK OFFICE
CERTIFICATE OF CORRECTION

PATENT NO. : 6,295,862 B1
DATED : October 2, 2001
INVENTOR(S) : Kurokawa et al.

Page 1 of 1

It is certified that error appears in the above-identified patent and that said Letters Patent is hereby corrected as shown below:

<u>Title page,</u>
Item [75] Inventors: please change third inventor "Satoshi Hudu" to
-- Satoshi Hada --.

Signed and Sealed this

Second Day of April, 2002

Attest:

JAMES E. ROGAN
*Attesting Officer*  *Director of the United States Patent and Trademark Office*